(12) United States Patent
Christensen

(10) Patent No.: US 8,248,316 B2
(45) Date of Patent: Aug. 21, 2012

(54) BODY RADIATION AND CONDUCTIVITY IN RF COMMUNICATION

(75) Inventor: Craig L. Christensen, Pocatello, ID (US)

(73) Assignee: Semiconductor Components Industries, LLC, Phoenix, AZ (US)

( * ) Notice: Subject to any disclaimer, the term of this patent is extended or adjusted under 35 U.S.C. 154(b) by 1219 days.

(21) Appl. No.: 12/023,187

(22) Filed: Jan. 31, 2008

(65) Prior Publication Data

US 2008/0186241 A1 Aug. 7, 2008

(30) Foreign Application Priority Data

Feb. 1, 2007 (CA) .................................. 2576615

(51) Int. Cl.
*H01Q 1/12* (2006.01)
(52) U.S. Cl. ........................................ 343/718; 381/323

(58) Field of Classification Search ................... 343/718, 343/702; 381/323, 312, 23.1
See application file for complete search history.

(56) References Cited

U.S. PATENT DOCUMENTS

| | | | |
|---|---|---|---|
| 6,115,636 A | 9/2000 | Ryan | |
| 6,597,320 B2 * | 7/2003 | Maeda et al. | 343/718 |
| 2002/0190689 A1 | 12/2002 | Nakamura et al. | |
| 2006/0052056 A1 | 3/2006 | Park et al. | |
| 2010/0056956 A1 * | 3/2010 | Dufresne et al. | 600/586 |
| 2010/0321269 A1 * | 12/2010 | Ishibana et al. | 343/834 |

FOREIGN PATENT DOCUMENTS

| | | |
|---|---|---|
| EP | 1 263 114 A2 | 12/2002 |
| WO | 2007/066976 A1 | 6/2007 |
| WO | 2007/123343 A1 | 11/2007 |

\* cited by examiner

*Primary Examiner* — Hoanganh Le
(74) *Attorney, Agent, or Firm* — Pearne & Gordon LLP

(57) ABSTRACT

Method and System for wireless communications is provided. The system includes an RF module, and a coupler. The coupler is coupled with the RF module. The coupler includes a member for conductive coupling with the user's body such that RF energy is coupled into and/or out of the user's body.

37 Claims, 28 Drawing Sheets

BODY RADIATION AND CONDUCTIVITY IN RF COMMUNICATION

FIELD OF INVENTION

The present invention relates to Radio Frequency (RF) technology, and more specifically to a method and system for wireless communications associated with RF signals using a user's body.

BACKGROUND OF THE INVENTION

Modern wireless transceivers are becoming smaller and smaller while their features and uses are continuously increasing. An application of these miniature transceivers is a wireless enabled hearing aid. Wireless capabilities are becoming a desired feature of the hearing aids. The wireless capability may be used for a variety of functions such as device programming, user control, ear-to-ear communications and device synchronization. Body worn medical patch devices are another application of these miniature transceivers. These patch devices are becoming very useful for the treatment, and monitoring of disease. It is desired to provide a wireless capability in these medical devices for control and monitoring of the devices' function.

The physical size of a wireless antenna is generally an important factor of its performance. Physically small antennas generally have high losses and require more powerful transmitters and complex high sensitivity receivers for satisfactory performance. High power transmitters will be a problem due to the limited power available from the small batteries used in hearing aids and medical patch devices. The high sensitivity receivers often require more power and typically have a number of external components which will be difficult to fit within the small volume of the hearing aid or a medical patch device. As a result of the small physical size of the hearing aid and medical patch device the problem of devising an effective antenna for wireless communications is not adequately resolved by the prior art.

SUMMARY OF THE INVENTION

It is an object of the invention to provide a system and method that obviates or mitigates at least one of the disadvantages of existing systems.

In accordance with an aspect of the present invention, there is provided a system for wireless communications. The system includes a Radio Frequency (RF) module including an RF input, an RF output or a combination; and a coupler electrically coupled with the RF module. The coupler includes a conductive member for conductive coupling with the user's body when the system is in operation such that RF energy is coupled into and/or out of the user's body.

In accordance with another aspect of the present invention, there is provided a system for wireless commutations. The system includes a wireless communication device. The wireless communication device includes a Radio Frequency (RF) module having an RF port for RF communications, and a coupler coupling to the RF port and conductive coupling to a user's body so that at least a part of the user's body is used as a conductive path to an external wireless communication device.

In accordance with a further aspect of the present invention, there is provided a system for wireless commutations. The system includes a wireless communication device. The wireless communication device includes a Radio Frequency (RF) module having an RF port for RF communications, and a coupler coupling to the RF port and conductive coupling to a user's body so that at least a part of the user's body is used as an RF antenna for the wireless communications with an external wireless communication device.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
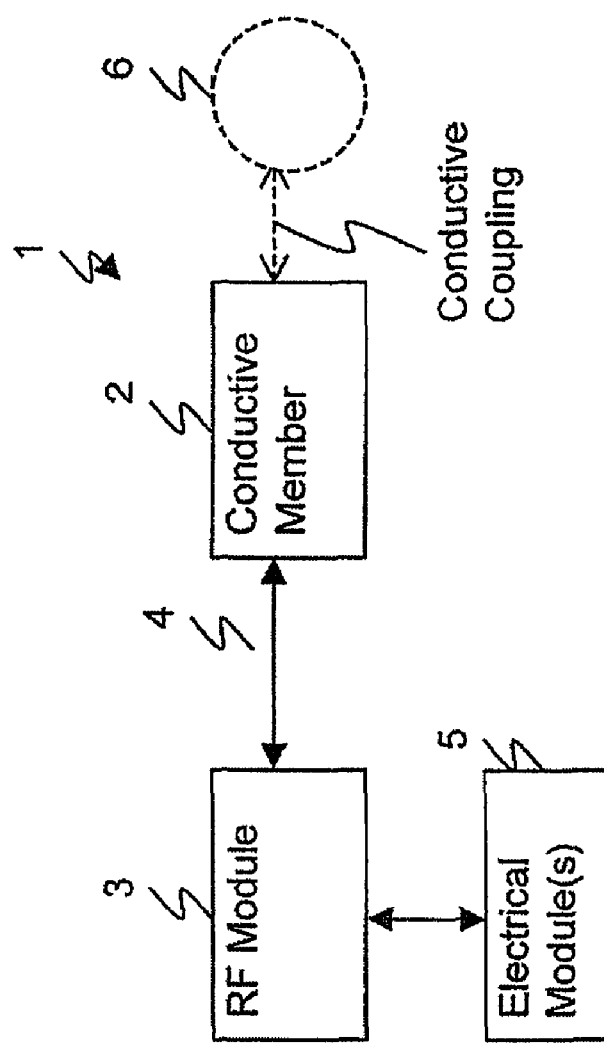
FIG. 1 is a schematic diagram illustrating a wireless device in accordance with an embodiment of the present invention.

Referring to FIG. 1, there is illustrated a wireless device in accordance with an embodiment of the present invention. The wireless device 1 of FIG. 1 includes a body coupler having a conductive member 2, and an RF module 3 having an RF input, an RF output or a combination thereof for wireless communications. The RF input/output may be the RF port of a wireless transmitter, the RF port of a wireless receiver, or the RF port of a transceiver's antenna.

The conductive member 2 is in physical contact or in close proximity with the skin of a living body 6 when the wireless device 1 is in operation. The physical contact or the close proximity implementation ensures a solid connection between the use's body and the RF module 3. The wireless device 1 may be worn on the body 6 so that the solid connection is accomplished when it is in operation. The conductive member 2 couples the living body 6 to the RF input, the RF output or a combination thereof in the RF module 3. In operation, the body 6 acts as a RF conductor (conductive path) of the RF energy or a pseudo antenna (radiator, collector).

In the description, the terms "living body", "body" and "user's body" are used interchangeably, and indicate a body of a living matter, such as an animal or a human's body. In the description, the term "body" may indicate a part of the body or a whole body. In the description, the terms "connect (connected)" and "couple (coupled)" may be used interchangeably.

The conductive member 2 may include a contact surface or may be in or on a contact surface of the wireless device 1. The user's body 6 contacts to the contact surface when the wireless device 1 is in operation. The contact surface may be a part of a shell, a housing, a case, or a cover of the wireless device 1. In the description, the terms "shell", "housing", "case", and "cover" are used interchangeably, and indicate an object for partially or fully covering (housing, casing, enclosing) one or more elements. The contact surface may be a part of a body coupling member for fitting at least a part of the wireless device 1 into the user's body 6.

The conductive member 2 may be, but not limited to, metallic, conductive elastomers, conductive plastics, conductive paints/coating, conductive mesh, conductive webs, conductive screens, conductive liquids or gels.

The body coupler may further include one electrical connection 4 (e.g., electrode, contact) connected to the RF module 3. The electrical connection 4 between the conductive member 2 and the RF module 3 allows RF energy to be coupled into or out of the user's body 6. No ground connection is made at the conductive member or the user's body. In the description, the terms "body coupler" and "conductive coupler" may be used interchangeably.

In FIG. 1, one conductive member 2 is shown as example. However, the wireless device 1 may include more than one conductive member 2. The wireless device 1 may include more than one connection 4 for more than one conductive member 2, respectively.

The wireless device 1 may include electrical module(s)/component(s) 5 other than the RF module 3. The conductive member 2 is electrically isolated from the electrical components 5. The electrical components 5 may be isolated by a non-conductive material member, e.g., housing, coating, painting.

The wireless device 1 may be, but not limited to, a wireless hearing device that is in contact with, for example, a part of a head, an ear or an ear canal. The wireless device 1 may be, but not limited to, a wireless audio device which is used with a body coupling device, such as headphones, earphones, earbuds, stereophones, or headsets. The wireless device 1 may be, but not limited to, a portable (e.g., handheld) wireless personal device (e.g., a pager, a cellular phone, a device for music/image contents). The wireless device 1 may be, but not limited to, a wireless medical device for implementing medical or therapy operation or measurement via the wireless communications.

When used as a conductive medium, the RF energy coupled into the user's body 6 can be detected at other locations on the user's body 6 providing a communications link comparable to a wireless link. When used as an antenna, the user's body 6 becomes an electromagnetic radiator or collector, with a significant increase in physical size over the much smaller conductive coupling element. The RF energy is coupled from a wireless transmitter to the user's body 6 and conversely RF energy captured by the user's body 6 can be coupled into a wireless receiver. For example, an electrical conductor that is physically much smaller than the typically required minimum length of ¼ wavelength for an effective RF antenna can be used to couple the RF energy into the user's body.

Figure 2:
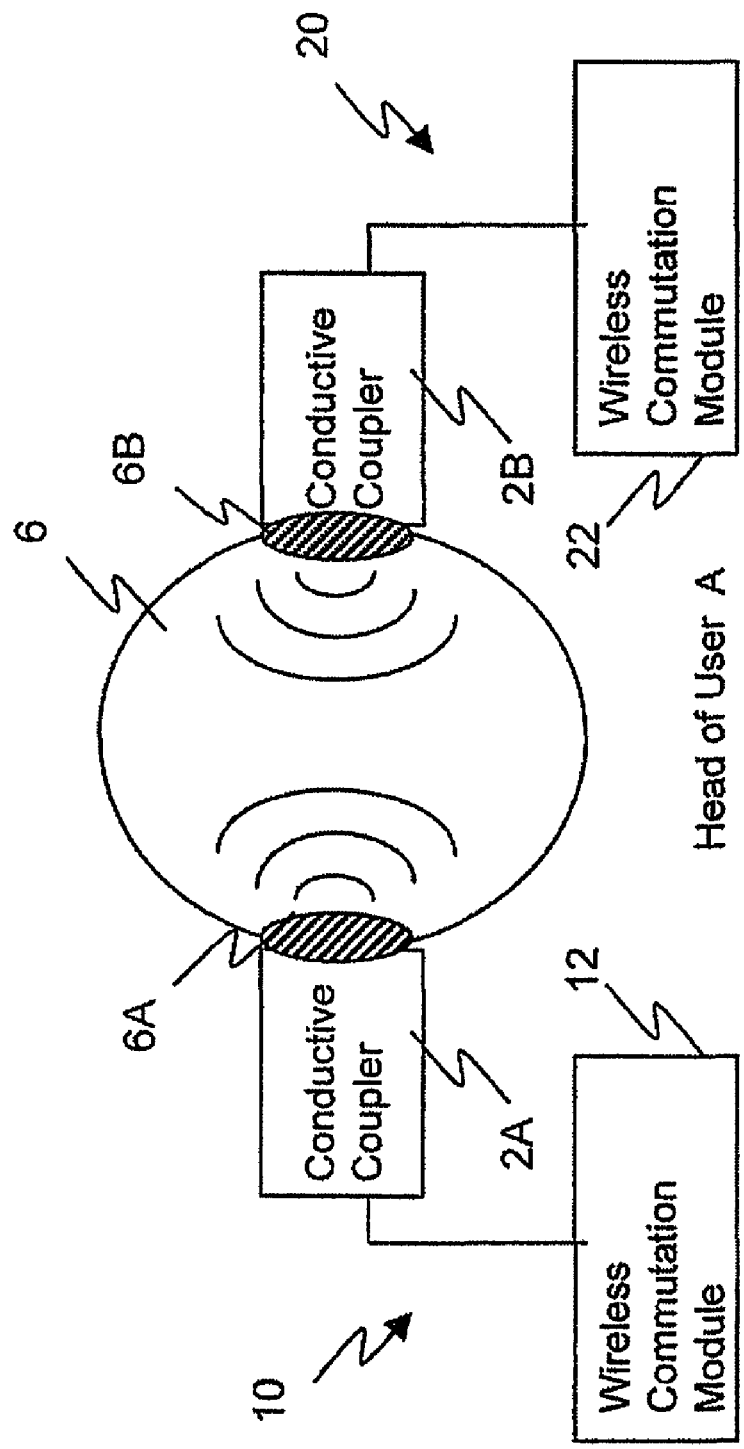
FIG. 2 is a schematic diagram illustrating an exemplary operation scenario for the wireless device of FIG. 1 where body conductivity is utilized for wireless communications.
Figure 3:
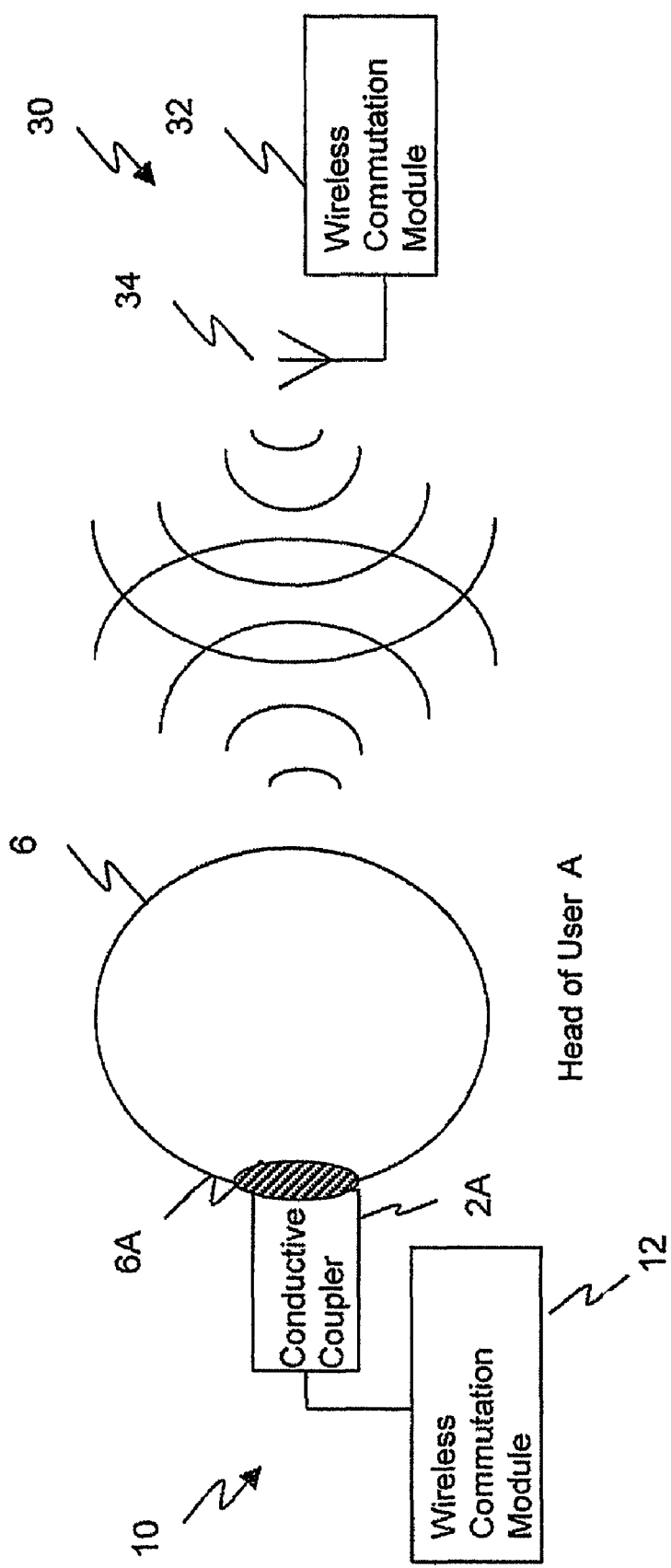
FIG. 3 is a schematic diagram illustrating another exemplary operation scenario for the wireless device of FIG. 1 where a body coupled pseudo antenna is utilized for wireless communications.
Figure 4:
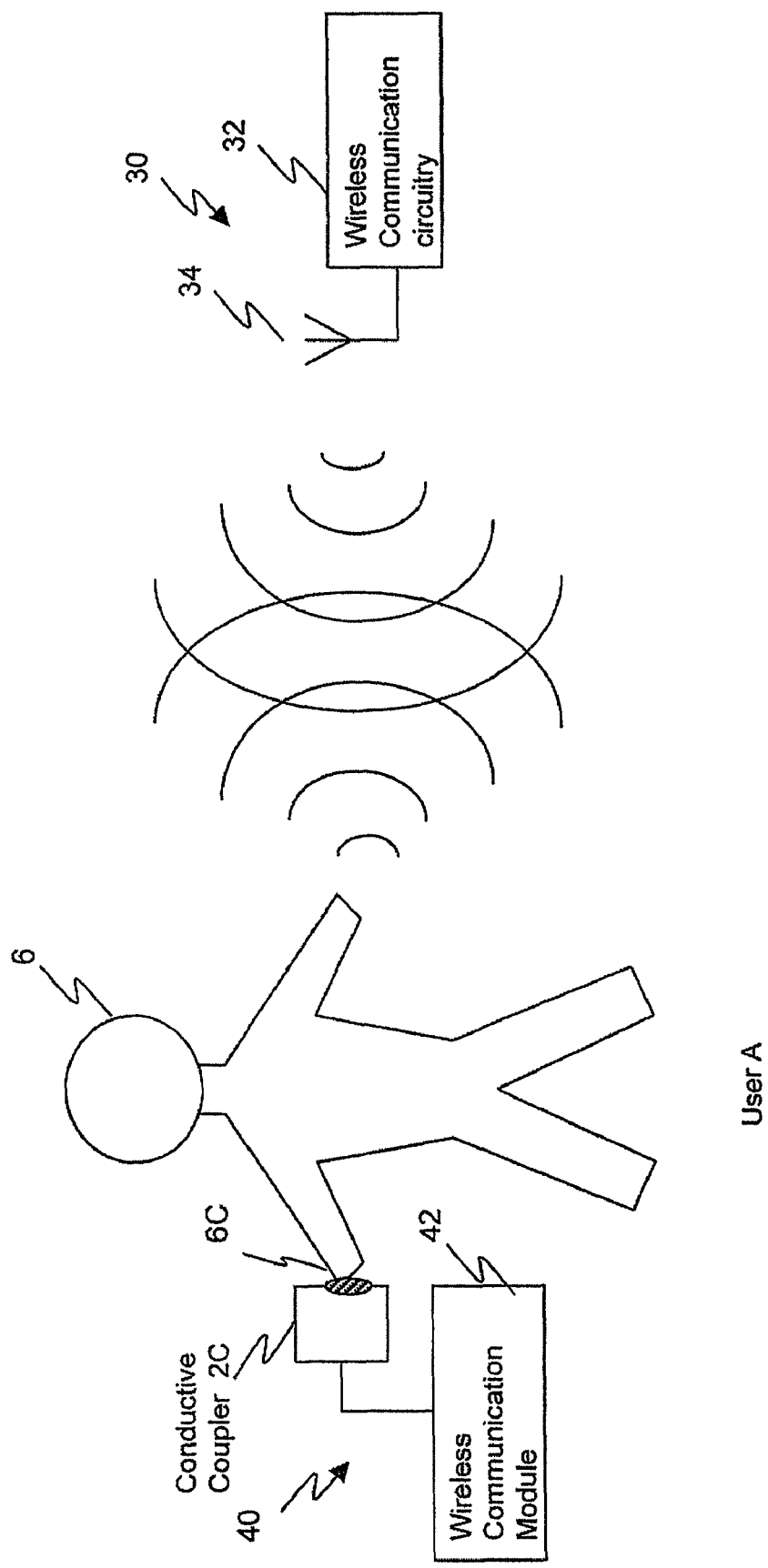
FIG. 4 is a schematic diagram illustrating a further exemplary operation scenario for the wireless device of FIG. 1 where the body coupled pseudo antenna is utilized for wireless communications.
Figure 5:
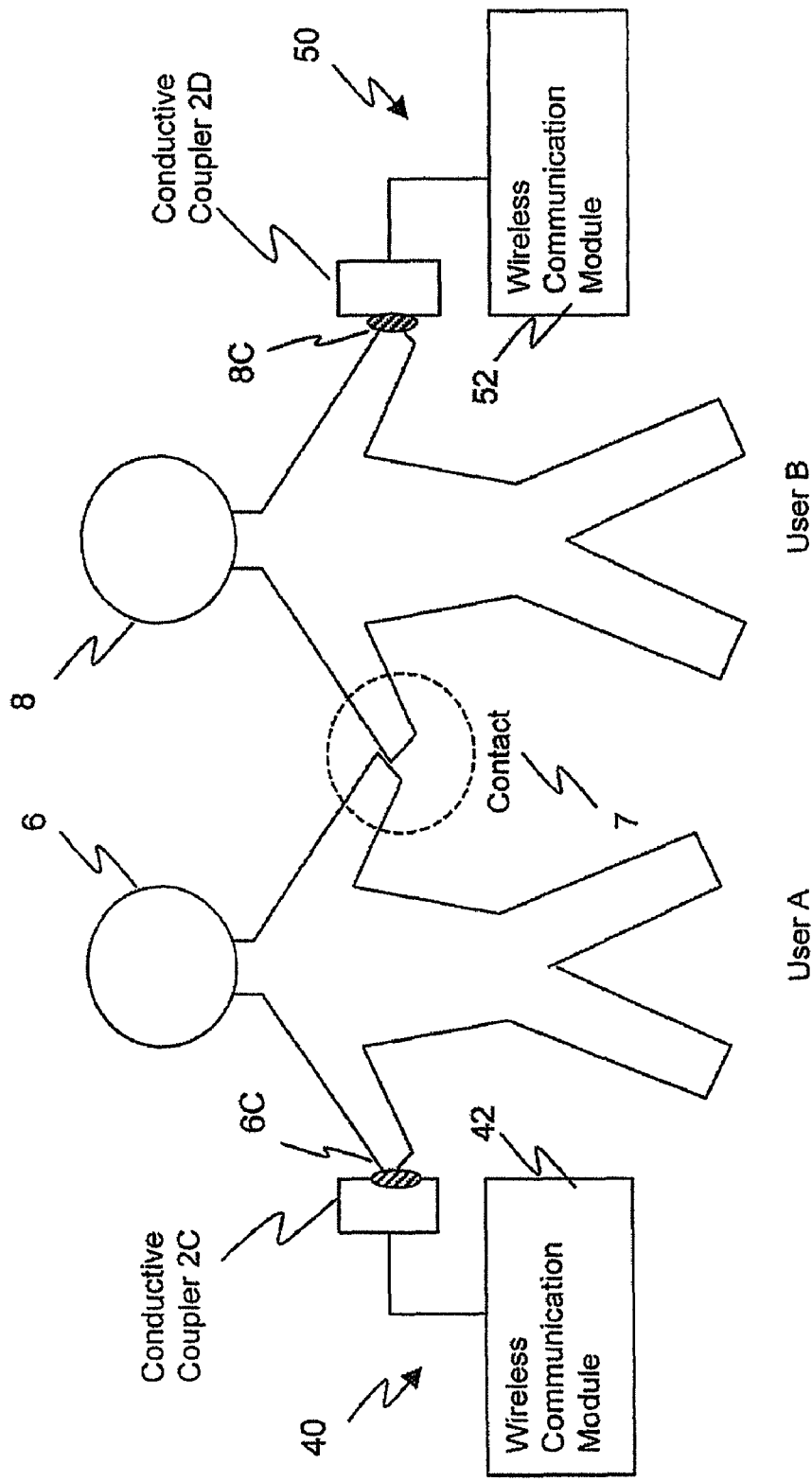
FIG. 5 is a schematic diagram illustrating a further exemplary operation scenario for the wireless device of FIG. 1 where the body conductivity is utilized for wireless communications.
Figure 6:
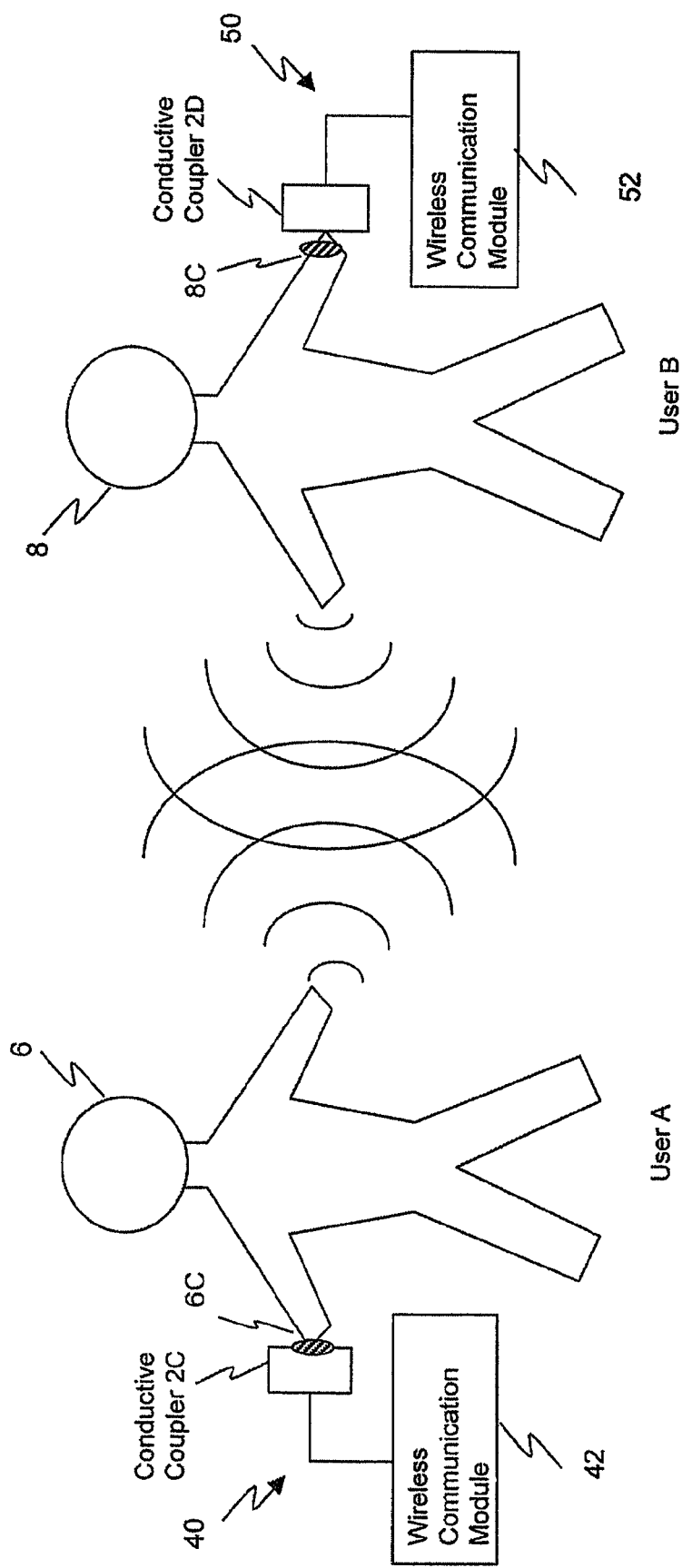
FIG. 6 is a schematic diagram illustrating a further exemplary operation scenario for the wireless device of FIG. 1 where the body coupled pseudo antenna is utilized for wireless communications.

Exemplary modes of operation for the wireless device 1 are shown in FIGS. 2-6. In a first mode of operation, wireless communications are implemented using body conductivity where the RF energy is conduced through the user's body to another wireless device that is also coupled to the user's body (FIGS. 2 and 5). For example, communications between a hearing aid and another hearing aid, and communications between a hearing aid and a handheld remote control device may be implemented by using the body conductivity. In a second mode of operation, the wireless communications are implemented using a body coupled pseudo antenna where the user's body acts as an antenna radiating and collecting the RF energy for wireless communications (FIGS. 3, 4 and 6).

In first and second operation modes, the overall antenna losses are significantly reduced when compared to the losses of physically small antenna. With reduced link losses the RF performance of the wireless device is improved. The reduced link losses also allow a reduction of the performance requirements for the wireless device without sacrificing overall link performance.

Testing was performed with small metallic coupling conductors whose dimensions were approximately 1/100 of the carrier wavelength. The physical size of these conductors was too small to be an effective antenna, however large enough to couple sufficient energy into or out of the user's body.

Referring to FIG. 2, there is illustrated an exemplary operation scenario for the wireless device 1 of FIG. 1 where the body conductivity is utilized for wireless communications. The wireless device 10 of FIG. 2 is worn on the body 6 of a user A. The wireless device 20 of FIG. 2 is also worn on the user's body 6 of the user A. Each of the body worn wireless devices 10 and 20 corresponds to the wireless device 1 of FIG. 1.

The wireless device 10 includes wireless communication module 12 (e.g., receiver, transmitter, transceiver, signal processor), and a conductive coupler 2A. The conductive coupler 2A is connected to the wireless communication module 12 or a part of the wireless communication module 12. The wireless device 20 includes wireless communication module 22 (e.g., receiver, transmitter, transceiver, signal processor), and a conductive coupler 2B. The conductive coupler 2B is connected to the wireless communication module 22 or a part of the wireless communication module 22.

The conductive coupler 2A corresponds to the conductive member 2 of FIG. 1. The conductive coupler 2A is in physical contact with a part 6A of the user's body 6. The conductive coupler 2B corresponds to the conductive member 2 of FIG. 1. The conductive coupler 2B is in physical contact with a part 6B of the user's body 6. In FIG. 2, the contacting portions 6A and 6B are parts of a head, and may be ears or ear canals.

The wireless devices 10 and 20 use the body coupling to couple the RF energy into or out of the contacting portions 6A and 6B. The contacting portions 6A and 6B and other portions of the user's body 6 between the contacting portions 6A and 6B are made of an intermediate conductive material, and thus form a conductive path between the wireless devices 10 and 20. In this example, the intermediate conductive material acts primary as an RF conductor. The wireless devices 10 and 20 communicate with each other through the contacting portions 6A and 6B.

The wireless device 10, 20 or both may be, but not limited to, wireless hearing devices. The wireless device 10, 20 or both may be hearing aids for improving the hearing ability of the user, and may be worn in the user's ear canals. Skin around the ear and in the ear canal has a much higher conductivity and less variation than other parts of the body, e.g., the skin of the hand. Thus the skin around the ear or ear canal will make the electrical coupling much more effective for the wireless devices.

The wireless device 10 may be a wireless audio device that is used with a body coupling device, such as headphones, earphones, earbuds, stereophones, or headsets. The wireless device 10 may be a wireless portable device or a medical patch device for medical or therapy operation or measurement. The wireless device 20 may be same or similar to the wireless device 10.

Referring to FIG. 3, there is illustrated another exemplary operation scenario for the wireless device 1 of FIG. 1 where the body coupled pseudo antenna is utilized for wireless communications. In FIG. 3, the wireless device 10 communicates with an external wireless device 30. The external wireless device 30 includes wireless communication circuitry 32 for wireless communications (e.g., receiver, transmitter, transceiver, signal processor) and an antenna 34 coupled to the wireless commutation circuitry 32. The wireless device 10 communicates with the external device 30. For example, when the wireless device 10 is worn on the user's head, the user's head and portions of the user's body 6 acts as an electromagnetic radiator or pseudo antenna having a significant physical size. In communications from the external wireless device 30, the user's head acts as a receiving antenna or collector. Some of the energy captured by the user is coupled into the receiver of the wireless device 10.

Referring to FIG. 4, there is illustrated a further exemplary operation scenario for the wireless device 1 of FIG. 1 where the body coupled pseudo antenna is utilized for wireless communications. The wireless device 40 of FIG. 4 is worn on the body 6 of the user A. The body worn wireless device 40 corresponds to the wireless device 1 of FIG. 1. The wireless device 40 includes wireless communication module 42 (e.g., receiver, transmitter, transceiver, signal processor), and a conductive coupler 2C. The conductive coupler 2C is connected to the wireless communication module 42 or a part of the wireless communication module 42.

The conductive coupler 2C corresponds to the conductive member 2 of FIG. 1. The conductive coupler 2C is in physical contact with a part 6C of the user's body 6. In FIG. 4, the contacting portion 6C is the user's hand or user's finger(s). The wireless device 40 couples the RF energy into or out of the contacting portion 6C through the conductive coupler 2C. The contacting portion 6C and portions of the user's body 6 act as an electromagnetic radiator or pseudo antenna on the wireless device side of the wireless link providing a physically larger and much more efficient antenna. In communications from the external wireless device 30 to the wireless device 40, the user's body 6 acts as a receiving antenna. The wireless device 40 and the external device 30 communicate with each other through 6C.

The wireless device 40 may be, but not limited to, a portable (e.g., handheld) wireless personal device (e.g., a pager, a cellular phone, a device for music/image contents). The wireless device 40 may be, but not limited to, a wireless medical patch device for medical or therapy operation or measurement. The wireless device 40 may be same or similar to the wireless device 10 of FIG. 2.

Referring to FIG. 5, there is illustrated a further exemplary operation scenario for the wireless device 1 of FIG. 1 where the body conductivity is utilized for wireless communications. The wireless device 50 of FIG. 5 is worn on the body 8 of a user B. The body worn wireless device 50 corresponds to the wireless device 1 of FIG. 1.

The wireless device 50 includes wireless communication module 52 (e.g., receiver, transmitter, transceiver, signal processor), and a conductive coupler 2D. The conductive coupler 2D is connected to the wireless communication module 52 or a part of the wireless communication module 52. The wireless device 50 may be same or similar to the wireless device 40 of FIG. 4.

The conductive coupler 2D corresponds to the conductive member 2 of FIG. 1. The conductive coupler 2D is in physical contact with a part 8C of the user's body 8. In FIG. 5, the contacting portion 8C is the user's hand or user's finger(s). The wireless device 50 couples the RF energy into or out of the contacting portion 8C.

The user A is in physical contact with the user B at a contact point 7. The RF energy flows from one body 6 (8) to the other 8 (6), allowing the wireless device 40 (50) on one body to communicate with another wireless device 50 (40) on another body. The wireless devices 40 and 50 communicate with each other through the contact point 7.

Referring to FIG. 6, there is illustrated a further exemplary operation scenario for the wireless device 1 of FIG. 1 where the body coupled pseudo antenna is utilized for wireless communications. In FIG. 6, the user A having the wireless device 40 and the user B having the wireless device 50 are physically separated from each other. The wireless devices 40 and 50 couple the RF energy into or out of the contacting portions 6C and 8C, respectively. The user's body 6 (8) acts as an electromagnetic radiator or collector.

In FIGS. 1-6, the representation of the conductive coupler (i.e., 2, 2A-2D) is schematic only, and its shape, size and form may vary in dependence upon the system design requirements. The conductive coupler (i.e., 2, 2A-2D) may have, but not limited to, a conductive surface. The conductive surface may be, but not limited to, square, rectangular, round or flat. The conductive coupler (i.e., 2, 2A-2D) may include a plurality of conductive layers. Nearly any metal or conductive material may be used to form the conductive coupler. The conductive coupling with the user produces effective wireless communications.

In FIGS. 1-6, the representation of the contacting portion (i.e., 6A, 6B, 6C, 8C) is schematic only, and the actual shape and size of the contacting portion may vary in dependence upon the design of the corresponding conductive coupler (i.e., 2, 2A-2D).

It will be understood by one of ordinary skill in the art that the same principal is applicable to other types of body worn or portable, handheld wireless devices to improve wireless performance including antenna efficiency.

Hearing aids with the body conductivity and body coupled pseudo antenna for wireless communications are described in detail. Conventionally, hearing aids are built with shells or housings that are generally formed from plastics or a resin material because of their various advantages: the materials are lightweight; the materials resist attack by body oils and perspiration; the materials can be made in many colors; complex shapes can be easily custom made; the materials are electrical insulators, simplifying installation of the electrical components and batteries; and cured materials are non-toxic. Some hearing aids, such as Behind The Ear (BTE), In The Ear (ITE), In The Canal (ITC), and Completely In the Canal (CIC) hearing aids, have parts (e.g., shells, housings, earpiece shells) custom molded for each customer. These custom molded hearing aids have a common trait that a part of the hearing aid fits very closely within the ear. In most of the applications the hearing aid seals the ear canal completely forming a tight fit.

The wireless device 1 of FIG. 1 is, for example, a custom molded hearing aid having one or more than one contact surfaces as shown in FIG. 7-18. In the implementations of FIG. 7-18, a conductive member (i.e., 2 of FIG. 1) is employed, for example, in or on a contact surface to which the user's ear contacts. The conductive member remains in contact with the ear's skin to ensure the maximum signal transfer. The contact surface may be a single contact point. The single contact point may provide the necessary conductivity to improve wireless performance. The contact surface may be a surface of a custom molded shell, and the entire shell may be made conductive to ensure that sufficient energy is transferred to the user's body.

Figure 7:
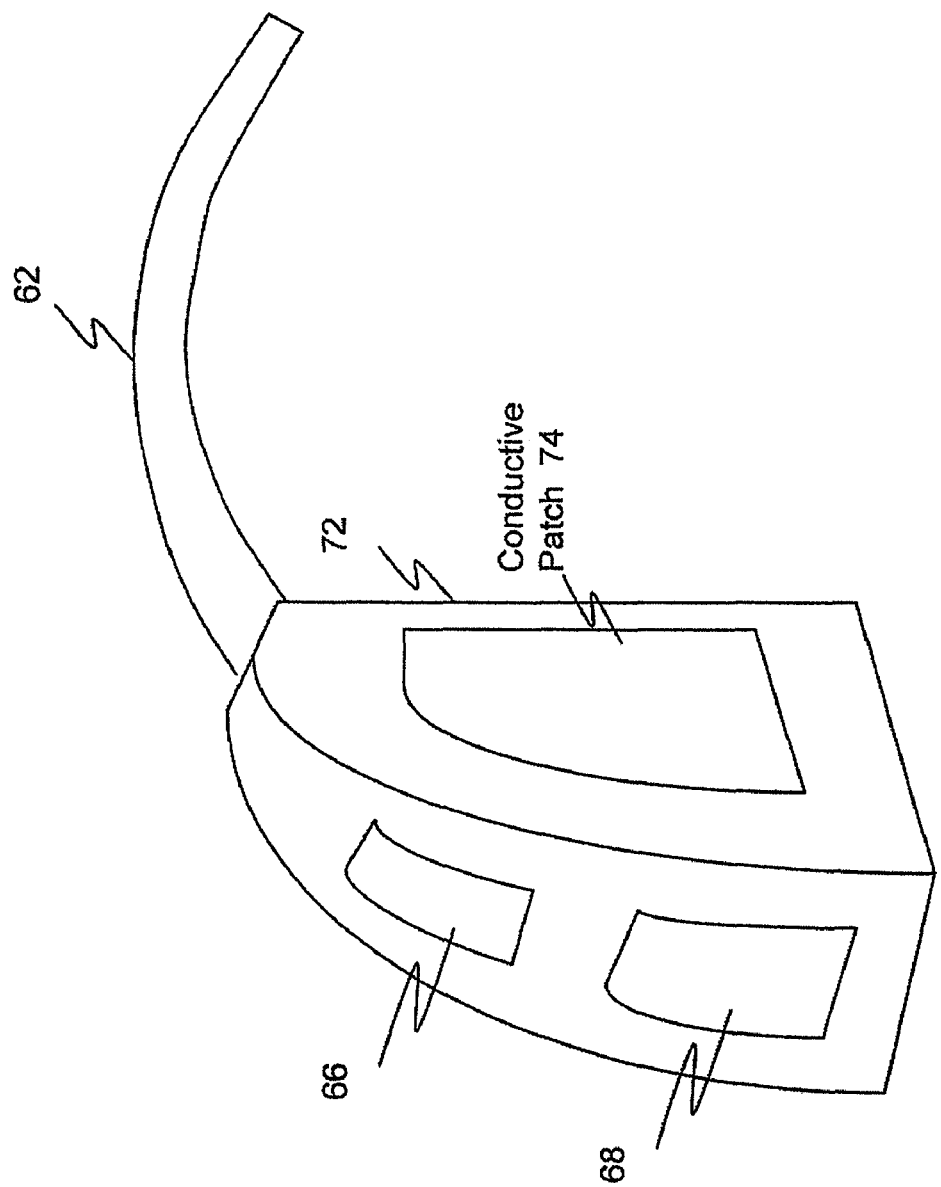
FIG. 7 is a perspective view of an example of the wireless device of FIG. 1.

Referring to FIG. 7, there is illustrated an example of the wireless device 1 of FIG. 1. The wireless device 60 of FIG. 7 is a standard form BTE hearing aid with a conductive member (hereinafter referred to as hearing aid 60). The hearing aid 60 corresponds to the wireless device 1 of FIG. 1. The hearing aid 60 includes a tone hook 62, electronics including microphone, a volume control 66, an on/off switch 68, a battery compartment (e.g., 86 of FIG. 9), and a main shell 72 for housing the electronics (e.g., 82, 84 of FIG. 9). An earpiece (not shown) on the tone hook 62 is custom molded to fit into a user's ear (e.g., 78 of FIG. 8).

The hearing aid 60 further includes a patch 74 having conductive material, hereinafter referred to as conductive patch 74. The conductive patch 74 corresponds to the conductive member 2 of FIG. 1. The conductive patch 74 may be molded into the main shell 72 or a part of the shell 72, or may be a conductive paint/coating, resin or a conductive mesh partially imbedded into the shell 72. A conductive mesh may be molded into the surface of the main shell 72 with enough surface area to make electrical contact to the body of the user.

Figure 8:
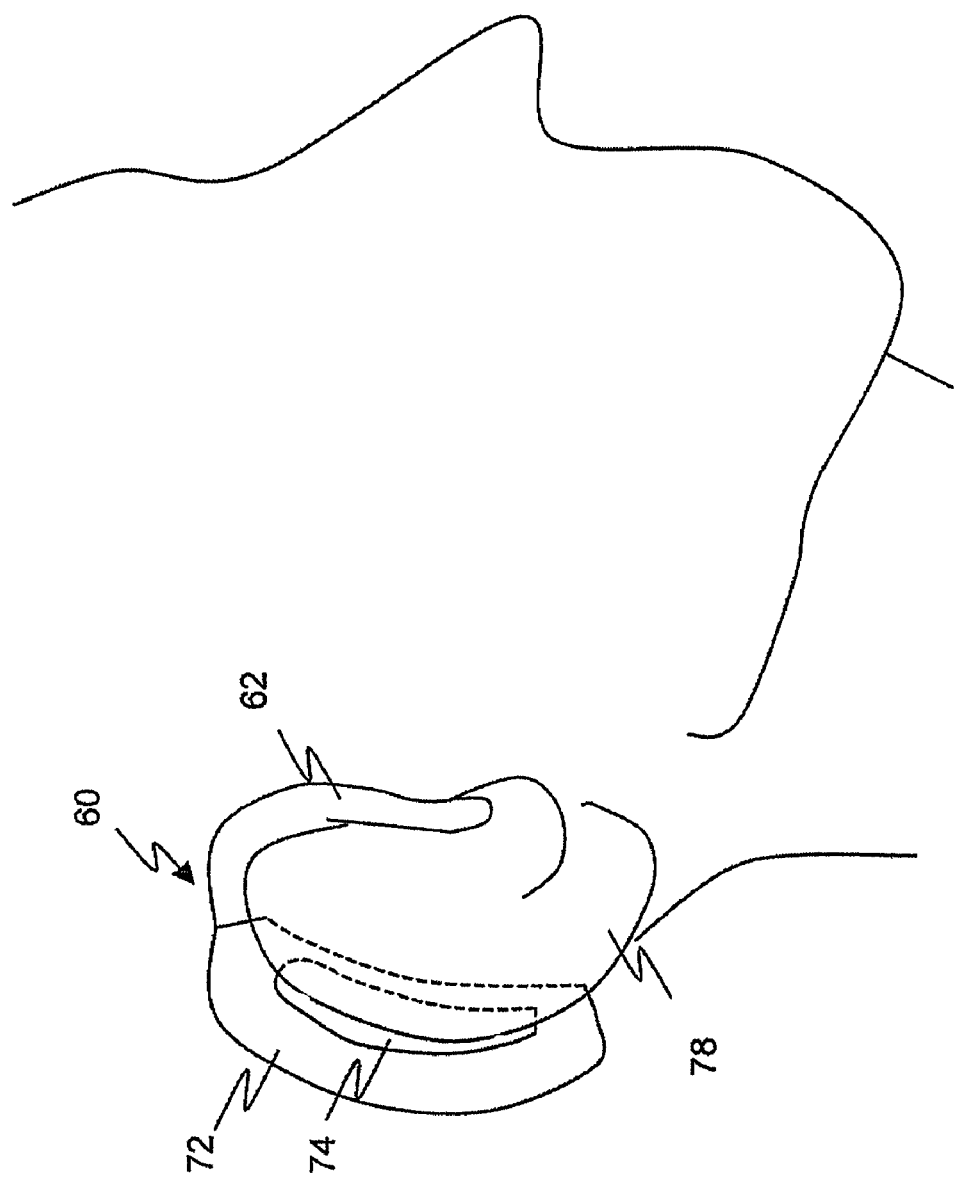
FIG. 8 is a side view of the wireless device of FIG. 7, relative to the user's right ear.

Referring to FIG. 8, there is illustrated the hearing aid 60 with the user's right ear. The main shell 72 is behind the ear 78 of a user. The section worn behind the ear 78 may be a standard shape and form. The conductive patch 74 is in contact with the skin of the user as shown in FIG. 8. The tone hook 62 provides amplified sounds to the earpiece (now shown) placed inside the ear 78.

Figure 9:
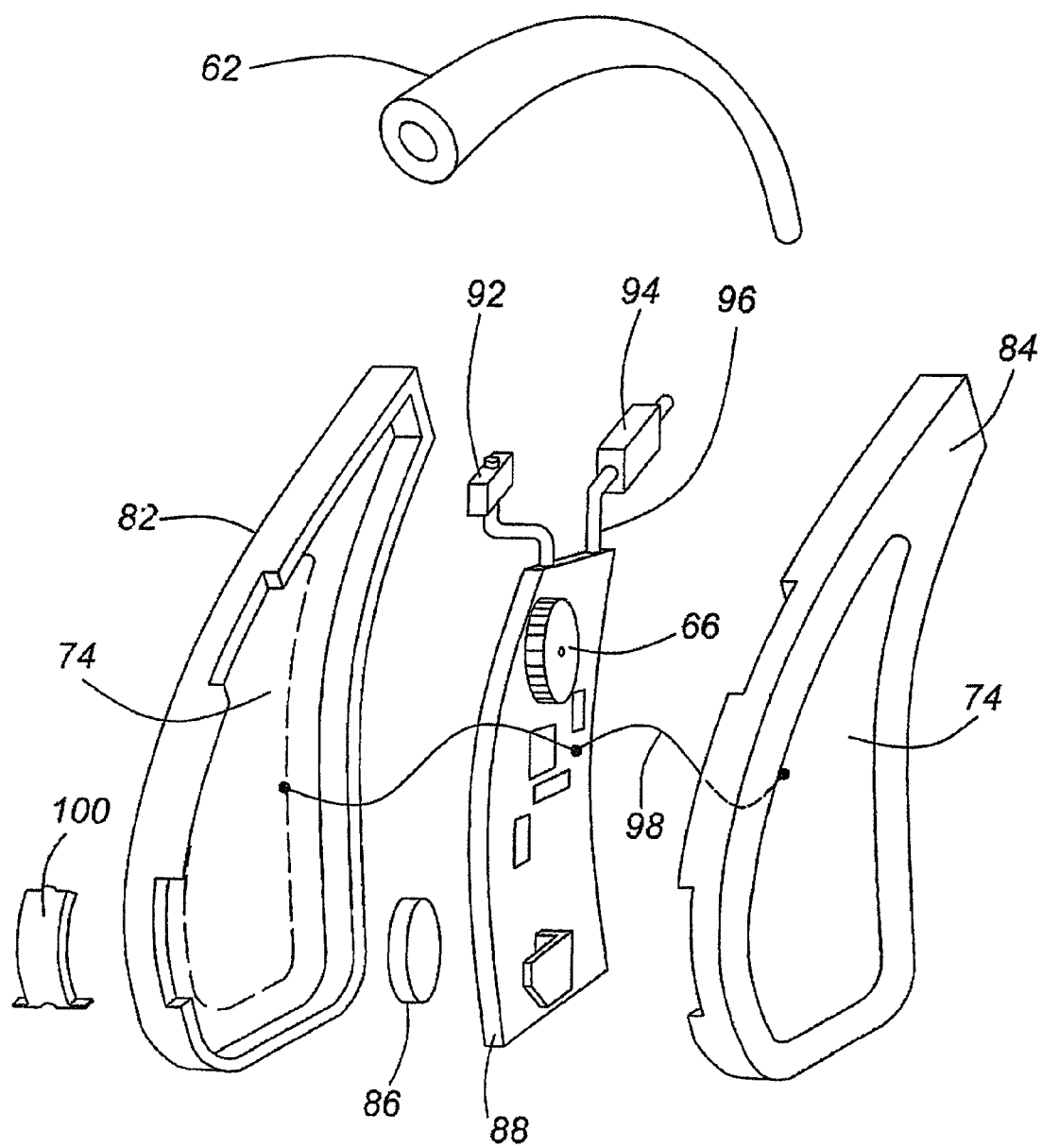
FIG. 9 is an exemplary exploded view of the wireless device of FIG. 7.

Referring to FIG. 9, there is illustrated an exemplary exploded view of the hearing aid 60 of FIG. 7. In FIG. 9, "82" represents one of shell pieces and "84" represents another shell piece, and the combination of the shell pieces 82 and 84 correspond to "72" of FIG. 7; "86" represents a battery; "88" represents an electronic module; "92" represents a microphone; "94" represents a receiver; "96" represents one or more interconnection wires; "98" represents an RF connecting cable; and "100" represents a battery door and corresponds to "68" of FIG. 7.

Figure 16:
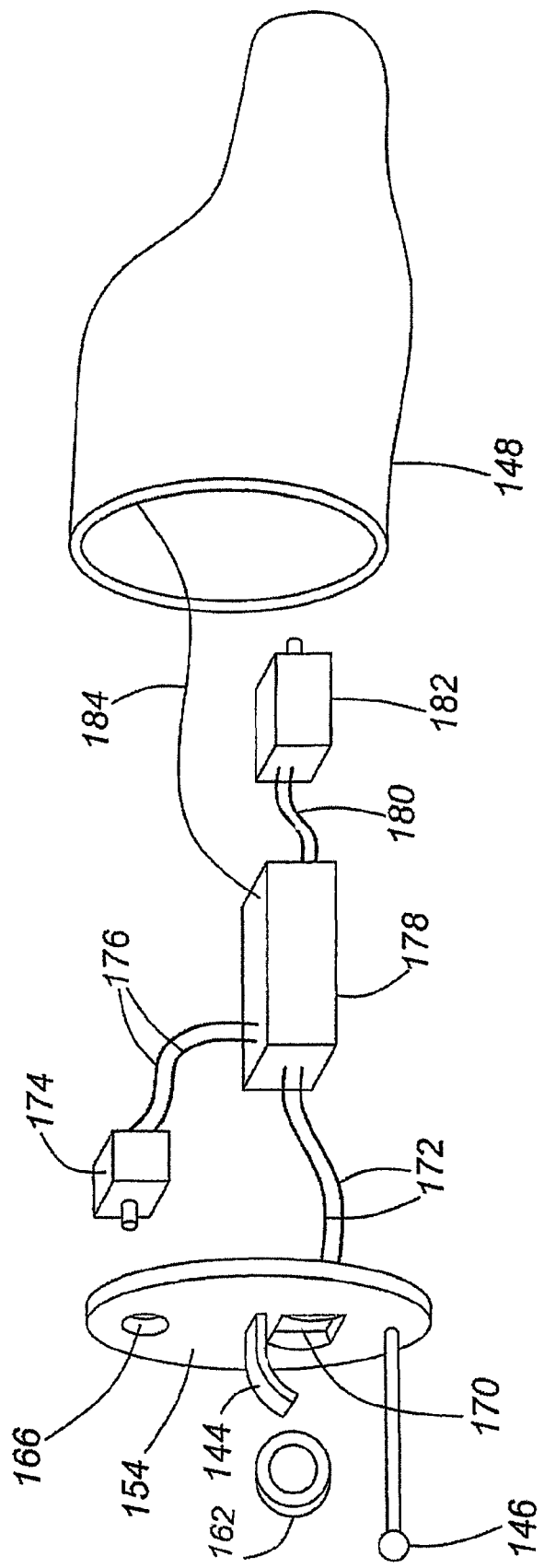
FIG. 16 is an exemplary exploded view of the wireless device of FIG. 14.
Figure 17:
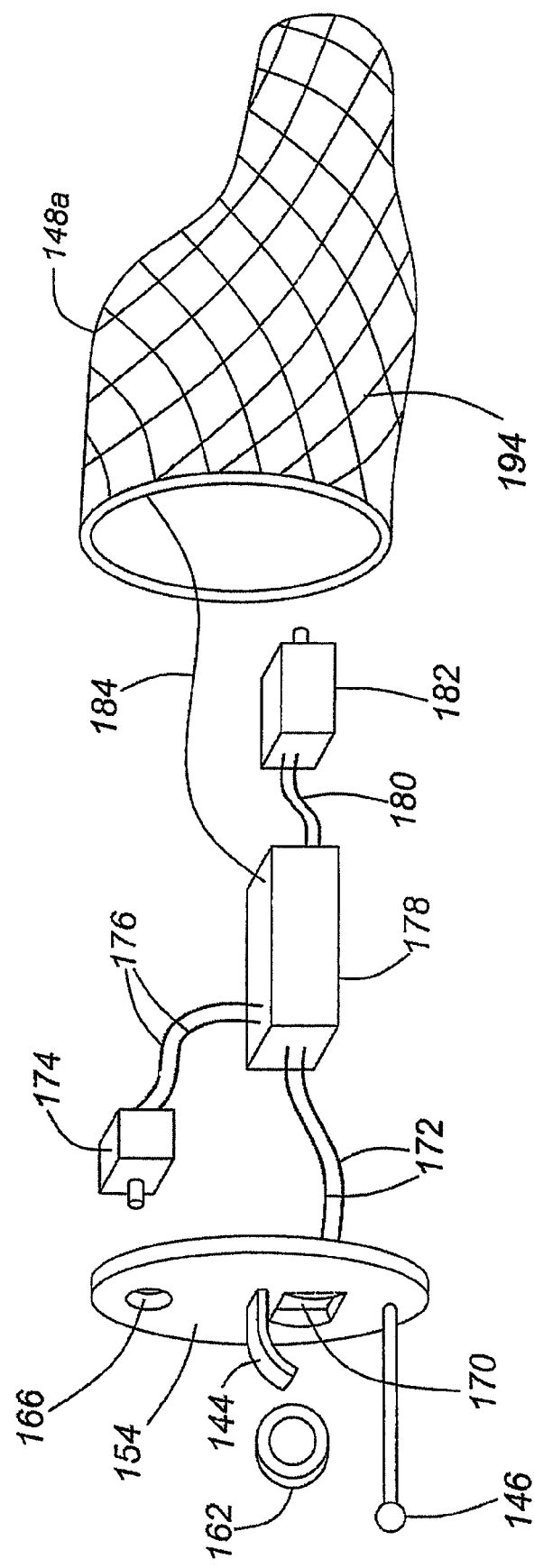
FIG. 17 is an exploded view of a further example of the wireless device of FIG. 1.
Figure 18:
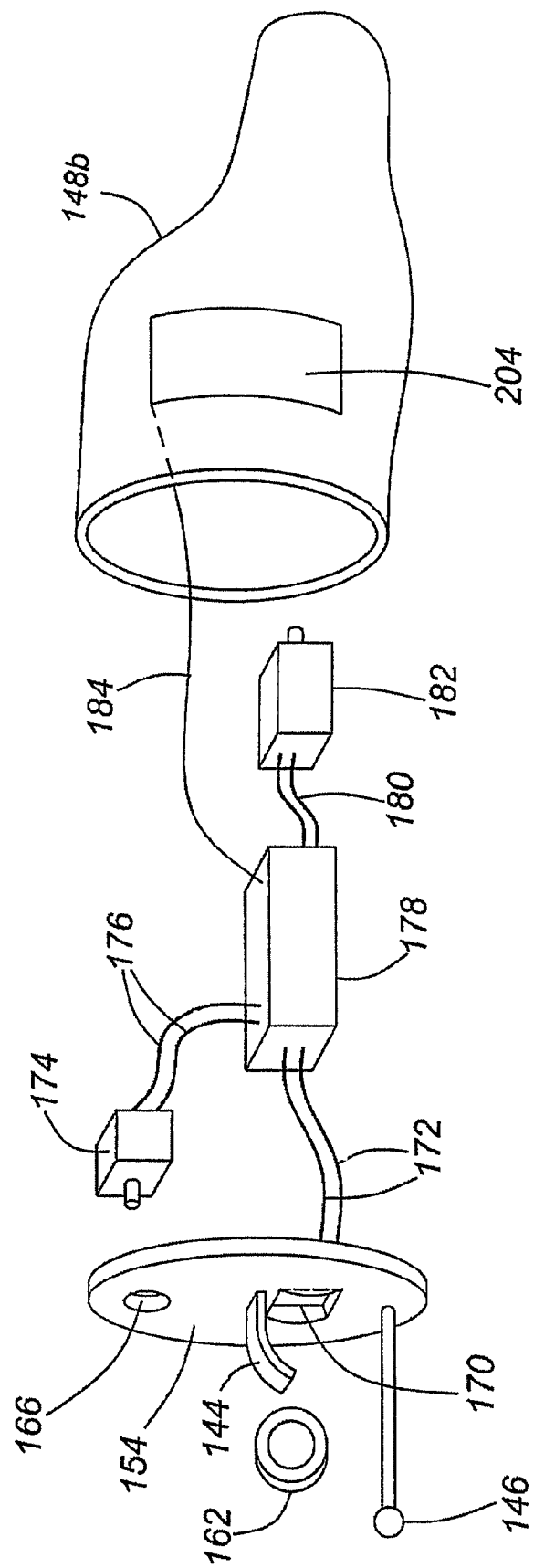
FIG. 18 is an exploded view of a further example of the wireless device of FIG. 1.

The electronic module 88 is housed in the shell pieces 82 and 84, which is typically constructed of non-conductive plastic. The shell piece (82, 84 or both) has a conductive patch 74 on the outside surface of the shell. The conductive patch 74 used for RF coupling on the custom molded shell may be constructed as a conductive patch as shown in FIG. 18, or a conductive coating as shown in FIG. 16, or a conductive mesh as shown in FIG. 17. The conductive patch 74 may be incorporated on both shell pieces 82 and 84 or may be incorporated on only one shell piece that is normally in contact with the users skin. The components inside are interconnected with the insulated wiring 96 and 98 to insure that during assembly of the hearing aid signals unwanted electrical contact is not made between the various components. The RF conducting cable 98 is a conductor, and is used to connect the RF port of the electronic module 88 and the conductive patch(s) 74 on the shell pieces 82 and/or 84.

Generally, BTE hearing aids are the largest of the modern hearing aids. They are however still physically too small to house an antenna that is large enough to have minimal losses. Using the conducting patch 74, effective wireless commutations can be accomplished without using a large antenna.

Figure 10:
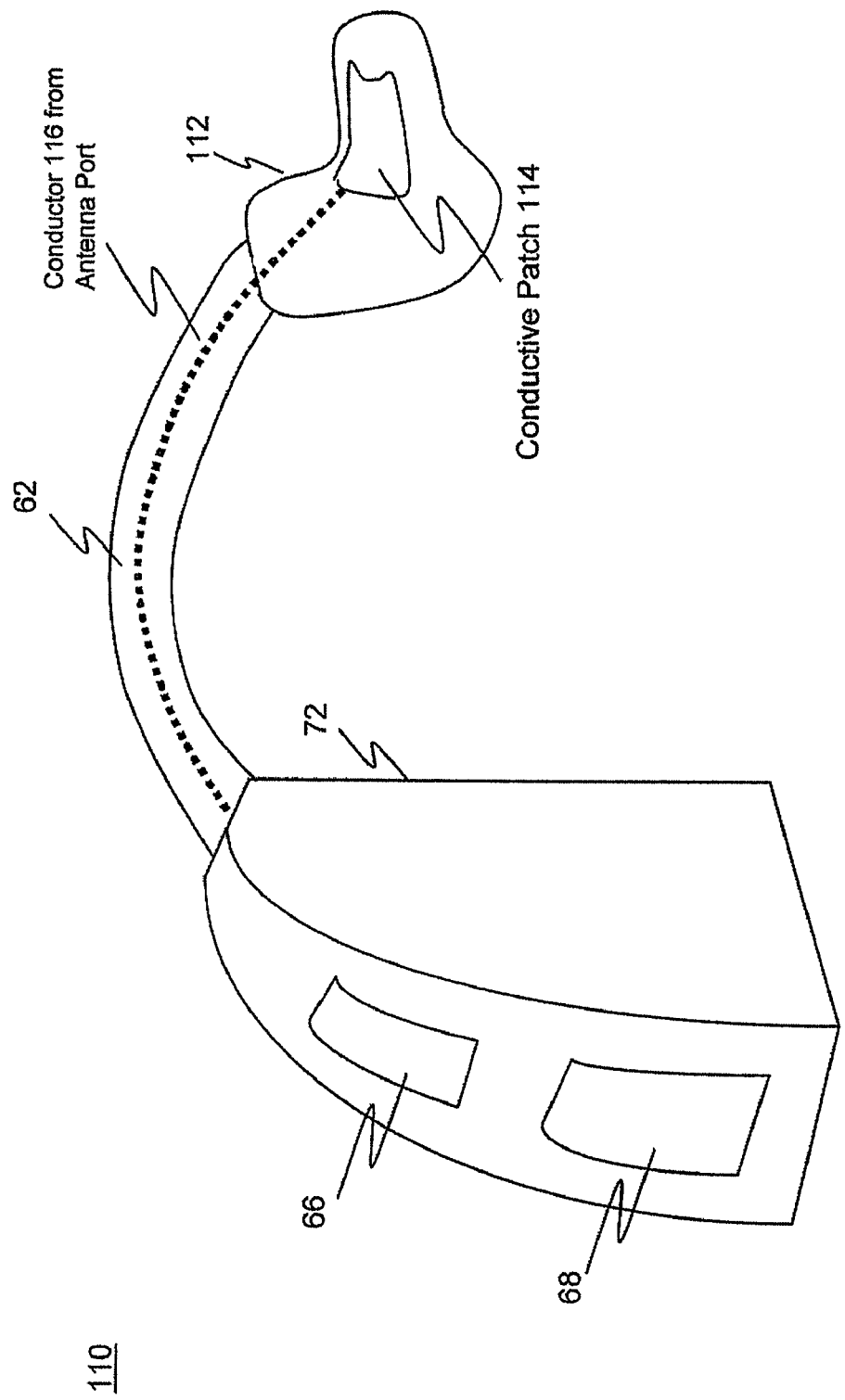
FIG. 10 is a perspective view of another example of the wireless device of FIG. 1.

Referring to FIG. 10, there is illustrated anther example of the wireless device 1 of FIG. 1. The wireless device 110 of FIG. 10 is a standard form BTE hearing aid with a conductive member (hereinafter referred to as hearing aid 110). The hearing aid 110 corresponds to the wireless device 1 of FIG. 1. In FIG. 10, a custom molded earpiece section (earpiece shell) 112 is connected to the end of the tone hook 62. A conductive patch 114 is in or on the earpiece section 112, and is connected to an RF connecting cable 116. The conductive patch 114 corresponds to the conductive member 2 of FIG. 1. The RF connecting cable 116 is a conductor. The RF connecting cable 116 is placed in the tone hook 62, and is connected to the RF port (e.g., antenna). In the description, the terms "earpiece 112", "earpiece section 112" and "(earpiece) shell 112" are used interchangeably.

The conductive patch 114 may be molded into the earpiece 112, or may be a conductive paint/coating, resin or a conductive mesh partially imbedded into the earpiece 112. A conductive mesh may be molded into the surface of the earpiece 112 with enough surface area to make electrical contact to the body of the user. The custom molded earpiece 112, which is made to fit tightly within the user's ear, ensures physical contact to the conductive material or patch when worn in normal fashion.

Figure 11:
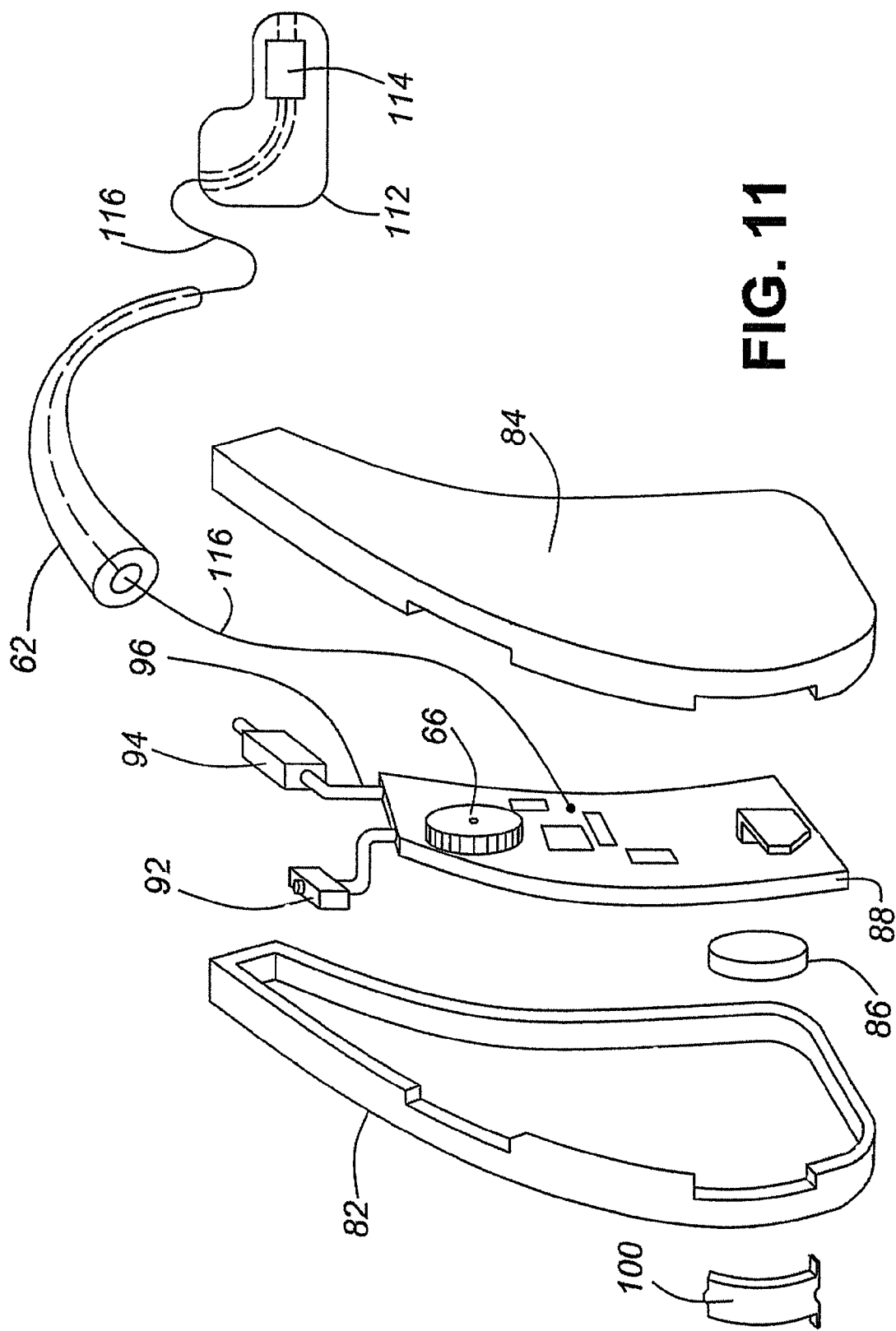
FIG. 11 is an exemplary exploded view of the wireless device of FIG. 10.

Referring to FIG. 11, there is illustrated an exemplary exploded view of the hearing aid 110 of FIG. 10. The view of FIG. 11 is similar to that of FIG. 9. The electronic module 88 is housed in the shell pieces 82 and 84, which is typically constructed of non-conductive plastic. The components inside are interconnected with insulated wiring 96 and 114 to insure that during assembly of the hearing aid, unwanted electrical contact is not made between the various components. The conductive patch 114 used for RF coupling on the custom molded earpiece may be constructed as a conductive patch as shown in FIG. 18, a conductive coating as shown in FIG. 16, or a conductive mesh as shown in FIG. 17. The RF connecting cable 114 is connected to the RF port of the electronic.

Similarly, the wireless device 1 of FIG. 1 may be a custom molded ITE, ITC or CIC hearing aid. ITE hearing aids generally sit flush within the ear. The ITE hearing aids are typically smaller than the BTE units. The exposed surface is called the faceplate and is generally cut to match the molded shell that fits within the ear. The electronics for the ITE hearing aid fit within the shell. ITC hearing aids also generally sit flush within the ear. The ITC hearing aids are smaller than the BTE and ITE hearing aids. Most of the ITC hearing aids fit within the ear canal of the user. As in the ITE hearing aid, the faceplate is a custom fit to the molded shell that is inserted into the ear canal. The electronics for the ITC hearing aids all fit within the molded shell. CIC hearing aids are the smallest hearing aids currently available. The CIC hearing aids are worn completely in the ear canal and often not visible at all. Because they are small and inaccessible the user cannot adjust the volume while the device is being worn, and no volume control is included. As in the ITE and ITC devices the end faceplate is modified to fit the custom molded body of the hearing aid. All the electronics fit within the shell that then fits within the ear canal.

Figure 12:
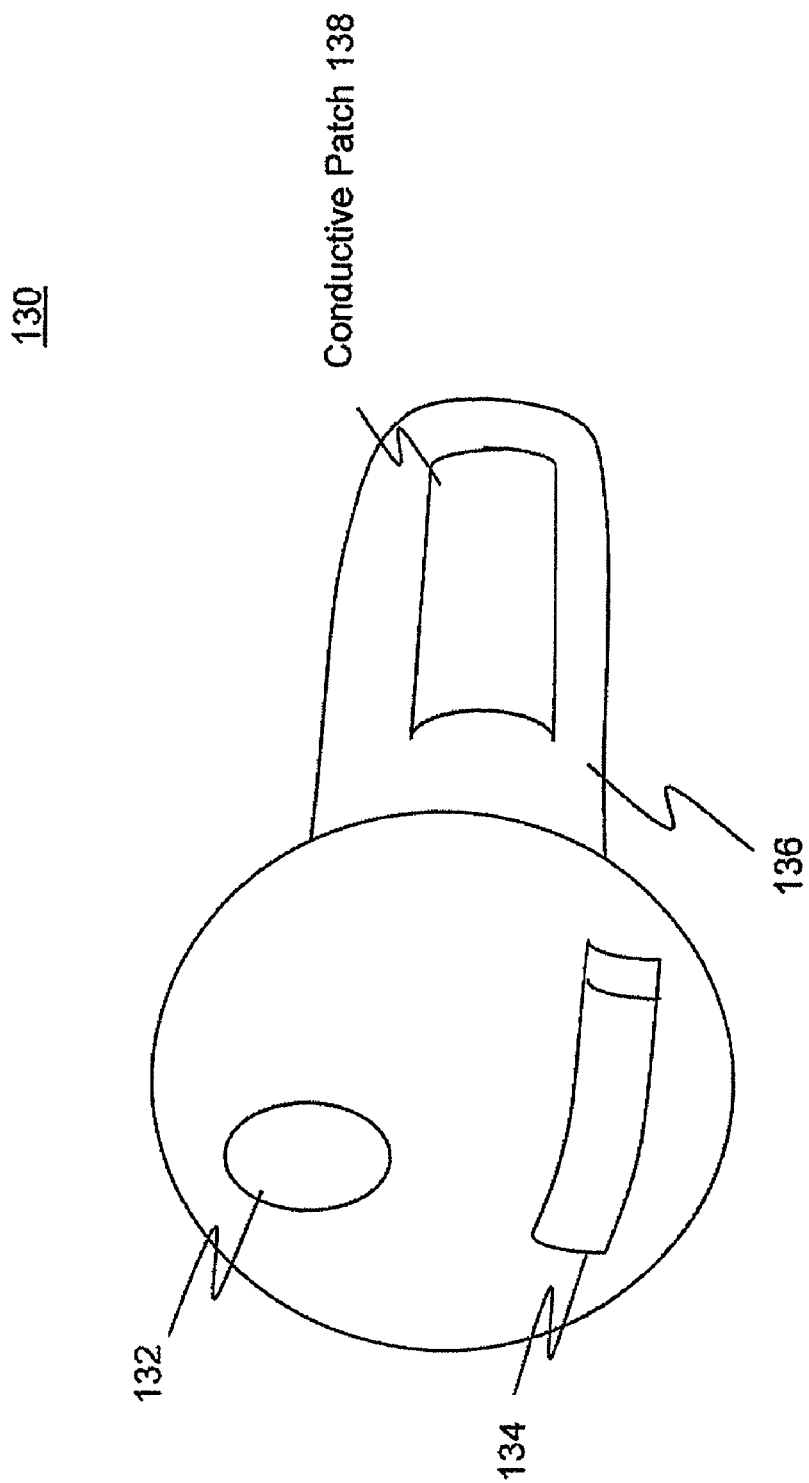
FIG. 12 is a perspective view of a further example of the wireless device of FIG. 1.

Referring to FIG. 12, there is illustrated a further example of the wireless device 1 of FIG. 1. The wireless device 130 of FIG. 12 is a custom molded hearing aid with a conductive member (hereinafter referred to as hearing aid 130). The hearing aid 130 is an ITE, ITC or CIC hearing aid device. The hearing aid 130 corresponds to the wireless device 1 of FIG. 1. The hearing aid 130 includes a battery door 132, a volume control 134, and a shell having a custom molded earpiece section (earpiece shell) 136. In the description, the terms "earpiece 136", "earpiece section 136" and "(earpiece) shell 136" are used interchangeably. A conductive patch 138 is molded into the earpiece section 136. The conductive patch 138 corresponds to the conductive member 2 of FIG. 1. The electronics for the hearing aid 130 fit within its shell. The conductive patch 138 may be connected to the antenna port of the hearing aid 130.

Figure 13:
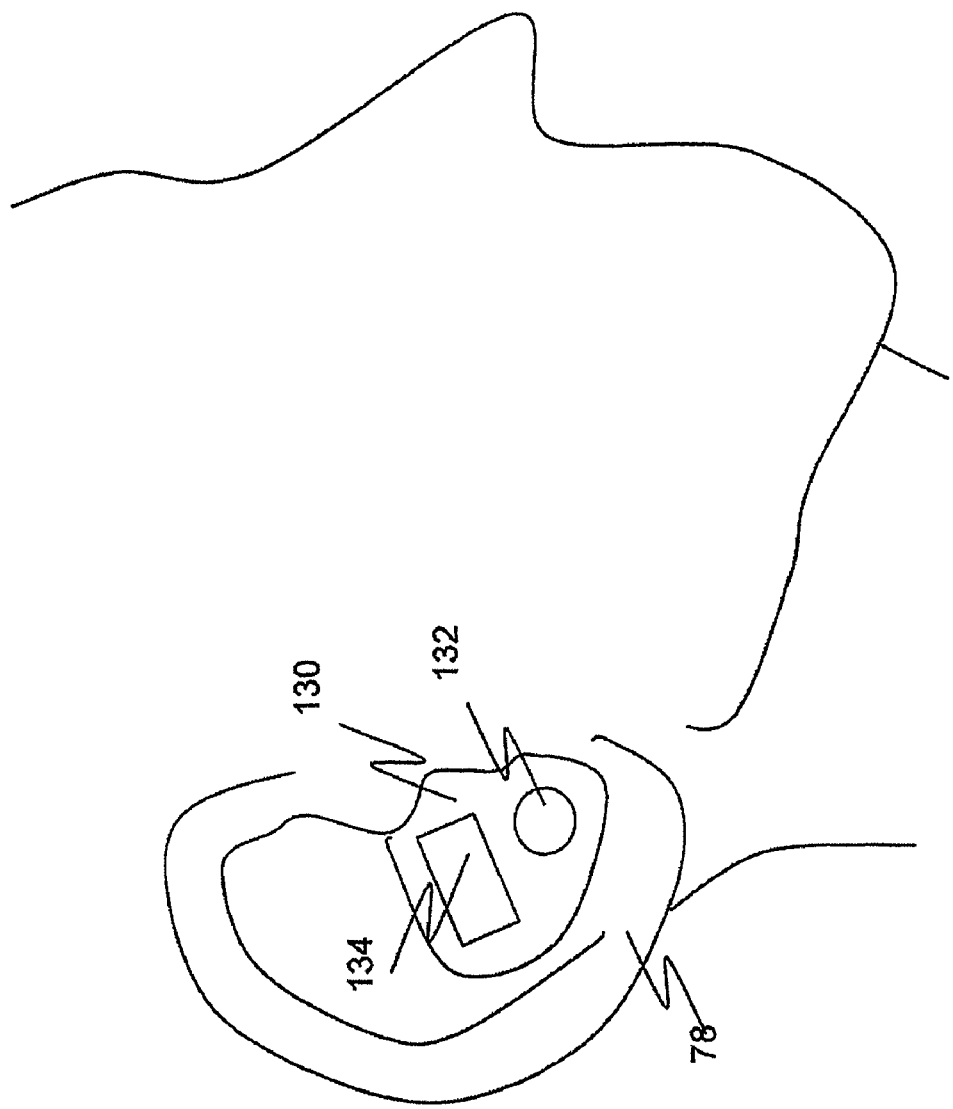
FIG. 13 is a side view of the wireless device of FIG. 12, in place within the user's right ear.

Referring to FIG. 13, there is illustrated the hearing aid 130 with the user's right ear. The earpiece section (136) is in the ear 78. The earpiece is custom molded to fit each individual user. When the hearing device 130 is worn in a normal operation, the conductive patch 138 of FIG. 12 is in contact with the skin of the user's ear.

Figure 14:
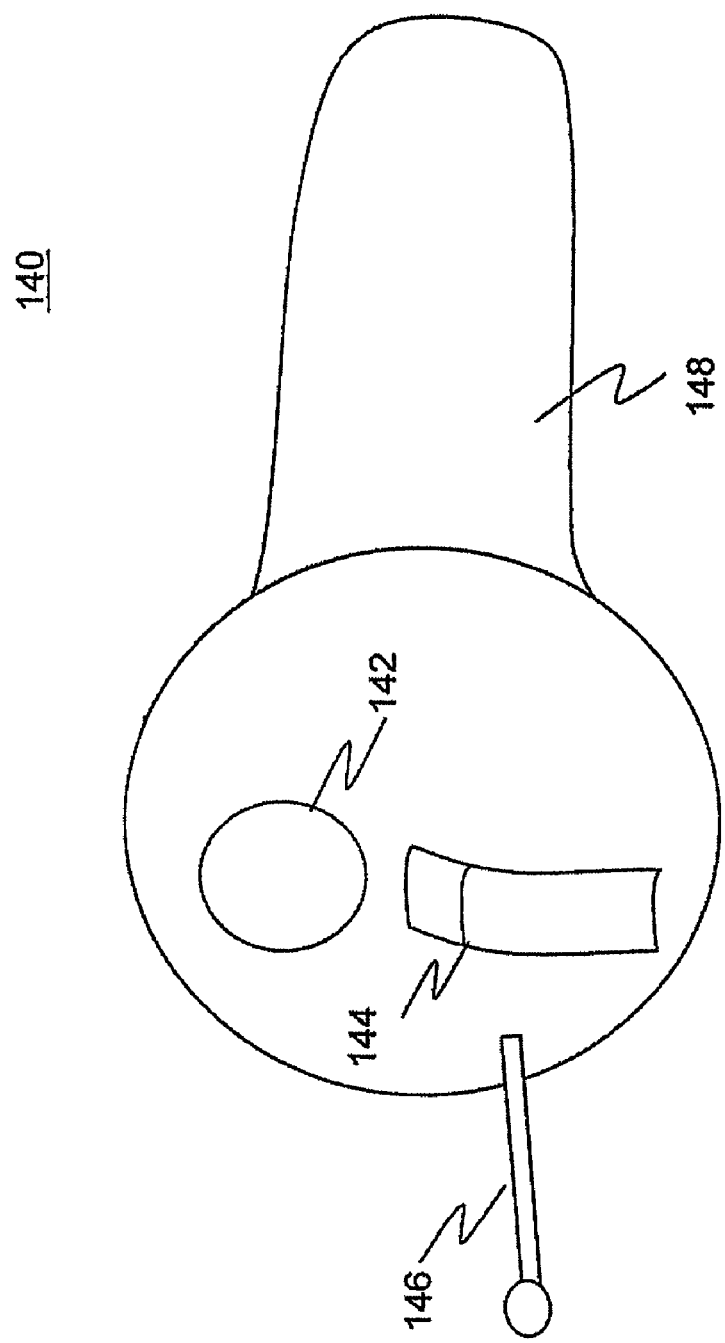
FIG. 14 is a perspective view of a further example of the wireless device of FIG. 1.

Referring to FIG. 14, there is illustrated a further example of the wireless device 1 of FIG. 1. The wireless device 140 of FIG. 14 is a custom molded CIC hearing aid with a conductive member (hereinafter referred to as hearing aid 140). The hearing aid 140 corresponds to the wireless device 1 of FIG. 1. The hearing aid 140 includes a microphone input 142, a battery door 144 and a retrieval line 146, and a shell having a custom molded earpiece section (earpiece shell) 148 with a conductive member that corresponds to the conductive member 2 of FIG. 1. The earpiece section 148 is in the user's ear in a normal operation, and is custom molded for each customer. The conductive member of the earpiece section 148 contacts to the use's ear when the hearing aid 140 is operated. In the description, the terms "earpiece 148", "earpiece section 148" and "(earpiece) shell 148" are used interchangeably.

The earpiece shell 148 may be partially or wholly coated with a conductive material, such as conductive paint or conductive resin. A conductive material may also be partially or wholly printed on the earpiece 148. The custom molded shell 148 may be a resin or plastic shell and the resin or plastic used to form the custom molded shell 148 may include a conductive material. A conductive flexible mesh may be partially or wholly on or in the shell 148. The conductive member may be in or on a part of the earpiece shell 148.

Figure 15:
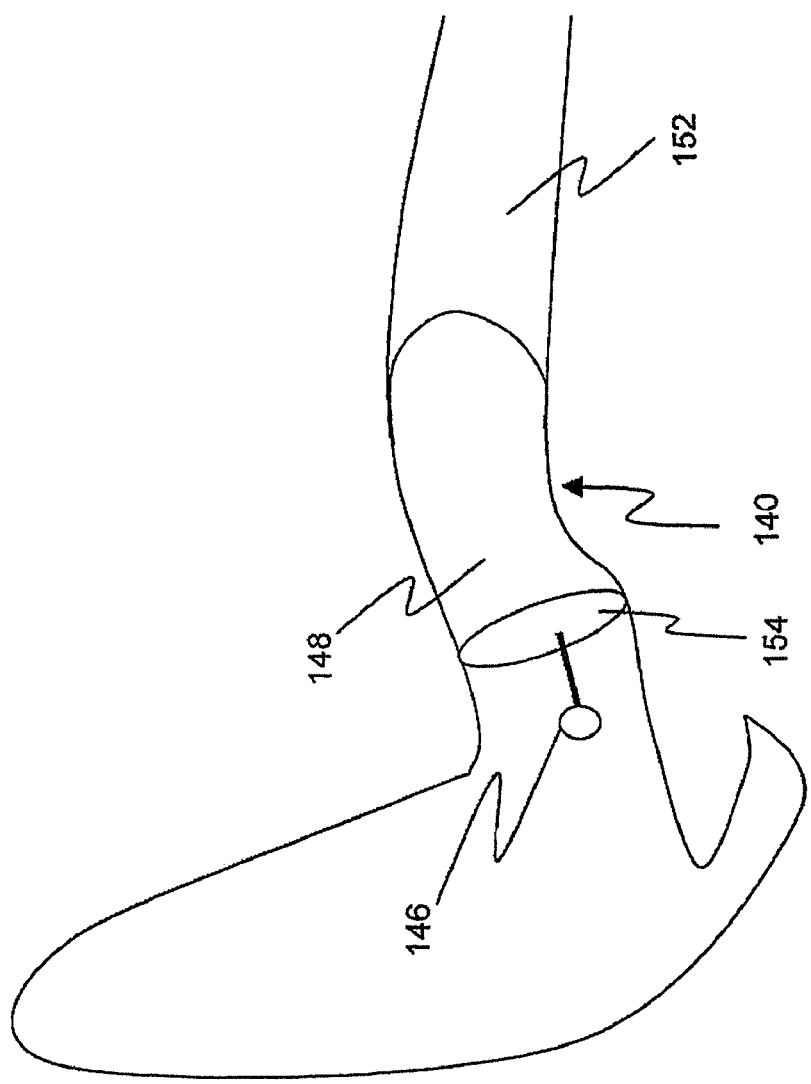
FIG. 15 is a side view of the wireless device of FIG. 14, in place within the user's right ear.

Referring to FIG. 15, there is illustrated the hearing aid 140 of FIG. 14 with the user's right ear. The shell 148 is custom molded for each user to fit within the ear canal 152 of the user. The end of a faceplate 154 is modified to fit the molded shell 148. The electronics for the hearing aid 140 all fit within the molded shell 148. When worn the conductive material on/in the shell 148 is in contact with the skin of the user's ear. The conductive material provides a connection between the RF port and the skin of the user as shown in FIG. 16.

FIG. 16 illustrates an exemplary exploded view of the hearing aid 140 of FIG. 14. In FIG. 16, "162" represents a battery; "166" represents a microphone port; "170" represents a battery compartment; "172" represents one or more wires from the battery; "174" represents a microphone; "176" represents one or more wires from the microphone 174; "178" represents an electronic module with RF; "180" represents one or more wires to 182; "182" represents a receiver (speaker); and "184" represents a wire from an RF port to a conductive coating on the shell 148.

The custom molded shell 148 is constructed in such a way that its outer surface is conductive. This may be accomplished with conductive paints, conductive coatings, a conductive mesh or a layer of conductive plastic molded on the outer surface of the shell 148. In all cases the interior surface of the shell 148 may be constructed out of non-conductive material. A conductive connection may be available on the interior of the shell 148 to allow for the electrical connection between the conductive coating and the transmitter/receiver port on the electronic module 178. This connection may be made with the insulated conductor (184) to prevent unwanted electrical contact between the various components within the hearing aid. The faceplate 154 is also made of non-conductive material. The electrical conductors (172, 176, 180, and 184) and the electronic module 178 are constructed with non-conductive coatings (except at the connection points) to minimize the possibility of unwanted electrical contact between the structures and components internal to the hearing aid, simplifying the assembly of the device.

FIG. 17 illustrates a further example of the wireless device 1 of FIG. 1. The wireless device of FIG. 17 is similar to the hearing aid 140 of FIG. 14, and includes an earpiece shell 148a with a contact mesh 194. The contact mesh 194 is in contact with the user's ear. The conductive mesh 194 may partially cover the earpiece shell 148a.

FIG. 18 illustrates a further example of the wireless device 1 of FIG. 1. The hearing aid of FIG. 18 is similar to the hearing aid 140 of FIG. 14, and includes an earpiece shell 148b with a contact patch 204. The conductive patch 204 partially covers the earpiece shell 148b. The contact patch 204 is in contact with the user's ear.

The wireless device 1 of FIG. 1 may be a custom molded wireless device other than those of FIGS. 6-18 or a non-custom molded wireless device (e.g., hearing assist devices, wireless audio devices using headphones, earphones, earbuds, stereophones, or headsets).

In some of these implementations, a conductive member (i.e., 2 of FIG. 1) may be formed as part of or molded into an ear clip, a frame, a headphone, an earphone, an earbud, a stereophone, or a headset.

In a further example, the conductive member may be formed in or on a moldable flexible or elastic member, such as an elastomer (seal) or flexible material, which contacts the user's skin. The elastomer or flexible material provides an improved custom fit for each individual or an audio seal for hearing devices. The elastomers typically used have similar properties of plastics or resins mentioned above, as they are lightweight and resistant to oils and perspiration, and can be made electrically conductive. The conductive elastomer seal or flexible material ensures physical contact with the user and coupling to couple RF energy into or out of the user's body.

Figure 19:
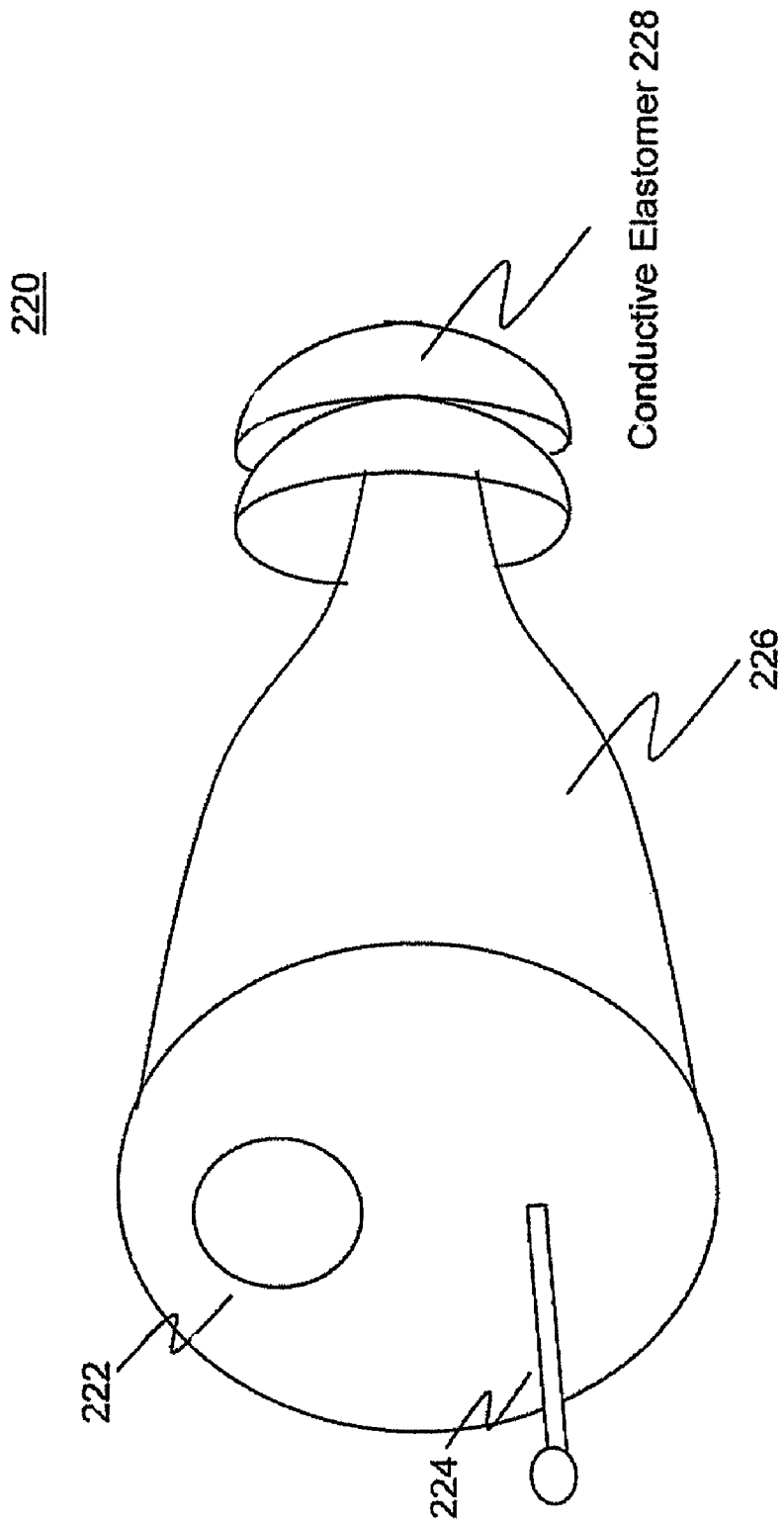
FIG. 19 is a perspective view of a further example of the wireless device of FIG. 1.

Referring to FIG. 19, there is illustrated a further example of the wireless device 1 of FIG. 1. The wireless device 220 of FIG. 19 is a non-custom molded hearing aid with a conductive member (hereinafter referred to as hearing aid 220). The hearing aid 220 corresponds to the wireless device 1 of FIG. 1. The hearing aid 220 includes a microphone 222 to pick up audio signals to be amplified and a retrieval line 224 to easily remove the hearing aid from the ear. The hearing aid 220 includes a non-custom molded shell 226 that has a general shape. The hearing aid 220 provides a simple amplification to the incoming signal without the custom fit and custom adjustment provided with a custom fit hearing aid.

A flexible conductive elastomer 228 is attached to the shell 226. The elastomer 228 seals the hearing aid in the user's ear. The elastomer seal 228 also acts as an acoustic barrier and helps retain the hearing aid 220 in place. Since the elastomer seal 228 is flexible and elastic in nature it is always be in tight contact with the skin of the ear. The elastomer seal 228 is made of a conductive material so that it can be used as the contact to couple RF energy into or out of the body. The elastomer seal 228 corresponds to the conductive member 2 of FIG. 1. The elastomer seal 228 with the conductive material ensures good contact with the user and the RF port of the hearing aid 220.

Figure 20:
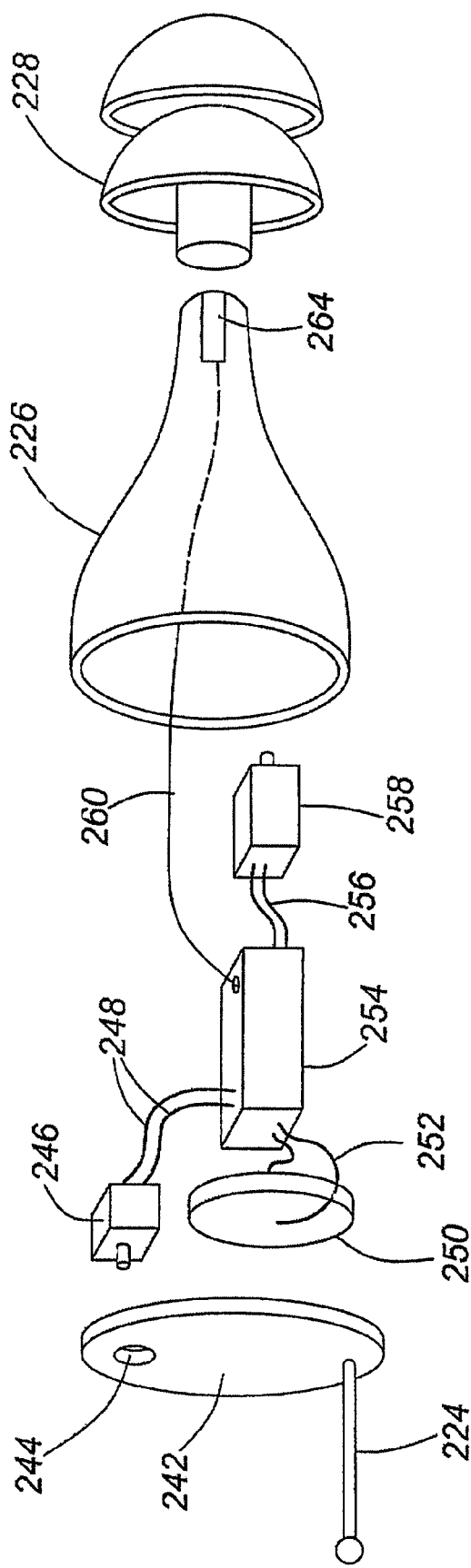
FIG. 20 is an exemplary exploded view of the wireless device of FIG. 19.

Referring to FIG. 20, there is illustrated an exemplary exploded view of the hearing aid 220 of FIG. 19. In FIG. 20, "242" represents a faceplate (endplate); "244" represents a microphone port; "246" represents a microphone and corresponds to 222 of FIG. 19; "248" represents one or more microphone wires; "250" represents a battery; "252" represents one or more battery wires; "254" represents an electronic module; "256" represents one or more receiver wires; "258" represents a receiver (speaker); "260" represents a wire from an RF port to an electrical contact; and "264" represents the electrical contact for a conductive ear seal.

In this instantiation the shell 226 is constructed from non-conductive plastic materials. The elastomer 228 is a conductive member and is used to couple RF energy to the user's body. The elastomer 228 is mounted on the non-conductive shell 226. An electrical connection to the transmitter/receiver is made through the electrical contact 264. The electrical contact 264 is a conductive member and is also electrically isolated by the shell 262. The electrical contact 264 provides the electrical connection between the transmitter/receiver port on the electronic module 254 and the conductive member 264. This connection may be made with an insulated conductor (260) to prevent unwanted electrical contact between the various components within the hearing aid. The faceplate 242 will also be made of non-conductive material. The electrical conductors (248, 252, 256, and 260) and the electronic module 254 are constructed with non-conductive coatings (except at the connection points) to minimize the possibility of unwanted electrical contact between the structures and components internal to the hearing aid, simplifying the assembly of the device.

Figure 21:
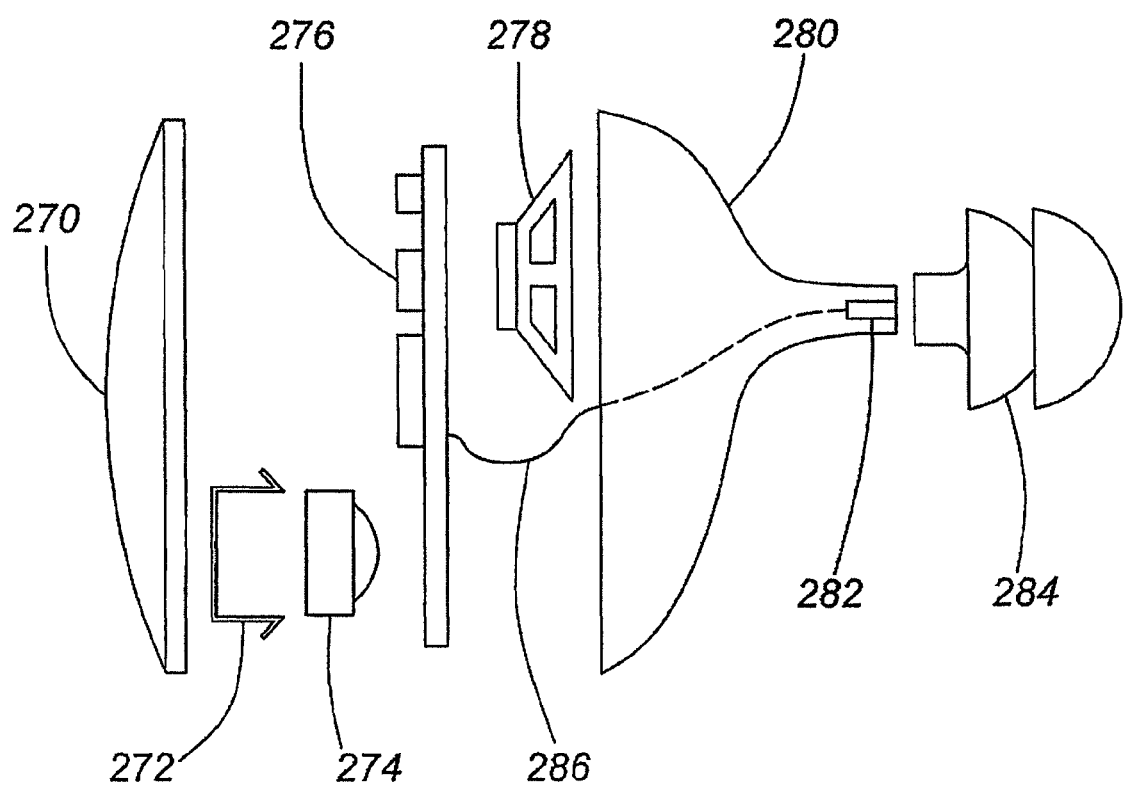
FIG. 21 is an exploded view of a further example of the wireless device of FIG. 1.

Referring to FIG. 21, there is illustrated a further example of the wireless device 1 of FIG. 1. The wireless device of FIG. 21 is a non-custom molded, earbud or monitor device. In FIG. 21, "270" represents an outside cover; "272" represents a battery clip; "274" represents a battery; "276" represents an electronic module including RF; "278" represents a speaker; "280" represents a non-conductive housing (shell) and corresponds to 226 of FIG. 20; "282" represents an electrical contact (a wire to a conductive ear seal) and corresponds to 264 of FIG. 20; "284" represents the conductive ear seal (conductive member) and corresponds to 228 of FIG. 19; and "286" represents a wire from RF port to the electrical contact.

In this instantiation the housing cover pieces 270 and 280 are constructed from non-conductive plastic materials. The conductive ear seal 284 is a conductive member and is used to couple energy to the body. The conductive ear seal 284 is mounted on the non-conductive housing 280, an electrical connection to the transmitter/receiver is made through the electrical contact 282. The electrical contact 282 is a conductive member, and is also electrically isolated by the non-conductive housing 280. The electrical contact 282 provides the electrical connection between the transmitter/receiver port of the electronic module 276 and the conductive member 284. The electronic module 276, the battery 274 and the speaker 278 are electrically insolated, as they are contained within the non-conductive housing cover pieces 270 and 280. Any interconnecting wires will also be insulated to prevent unwanted electrical contact between components.

Figure 22:
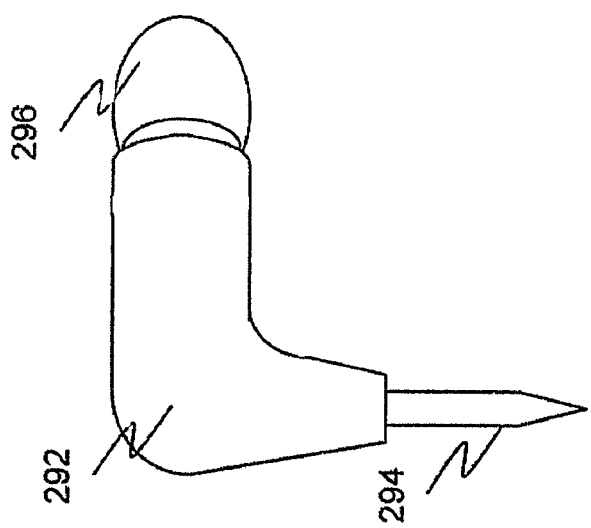
FIG. 22 is a perspective view of a further example of the wireless device of FIG. 1.

Referring to FIG. 22, there is illustrated a further example of the wireless device 1 of FIG. 1. The wireless device 290 of FIG. 22 is a non-custom molded, wireless earbud device for entertainment with a conductive member (hereinafter referred to as the earbuds device 290). The earbuds device 290 corresponds to the wireless device 1 of FIG. 1. The earbuds device 290 includes a body section 292, an antenna section 294 and a flexible conductive seal 296. The earbuds device 290 includes a speaker (not shown) placed in close proximity to the ear. The earbuds device 290 is placed outside of the ear canal. The flexible conductive seal 296 seals the ear canal and also acts as a conductive member (i.e., 2 of FIG. 1) that is in physical contact with the user's body.

In a further example, a small pad of conductive gel may be placed between the conductive member (i.e., 2 of FIG. 1) and the skin of the user to produce a good electrical contact with the user's skin. The conductive gel pad may be suited in applications where wireless communication devices may be worn as a patch on the skin of the user as described below.

Medical patch devices with the body conductivity and body coupled pseudo antenna for wireless communications are described in detail. Some medical patch devices (e.g., patch worn therapy or diagnostic/measurement systems) are beginning to become popular for a number of treatment and diagnostic regimes. In these applications a small electronic module contains the electronics that control regulate and even enhance drug delivery or perform a variety of diagnostic measurements for the patient. Wireless control or monitoring of these skin worn medical patch devices can greatly improve the patient's comfort and treatment. Efforts are underway to make these medical patch devices as small and unobtrusive as possible. Their construction likely focuses on lightweight, thin and flexible plastic materials to reduce cost and minimize patient discomfort. With the desired size limitations, these medical patch devices may suffer from poor antenna performance. Two common goals for the manufacturers of many of these devices are to make them inexpensive so they can be considered disposal and low power to maximize battery life. Similar challenges exist for incorporating wireless in the medical patch device as the wireless enabled hearing aid.

Figure 23:
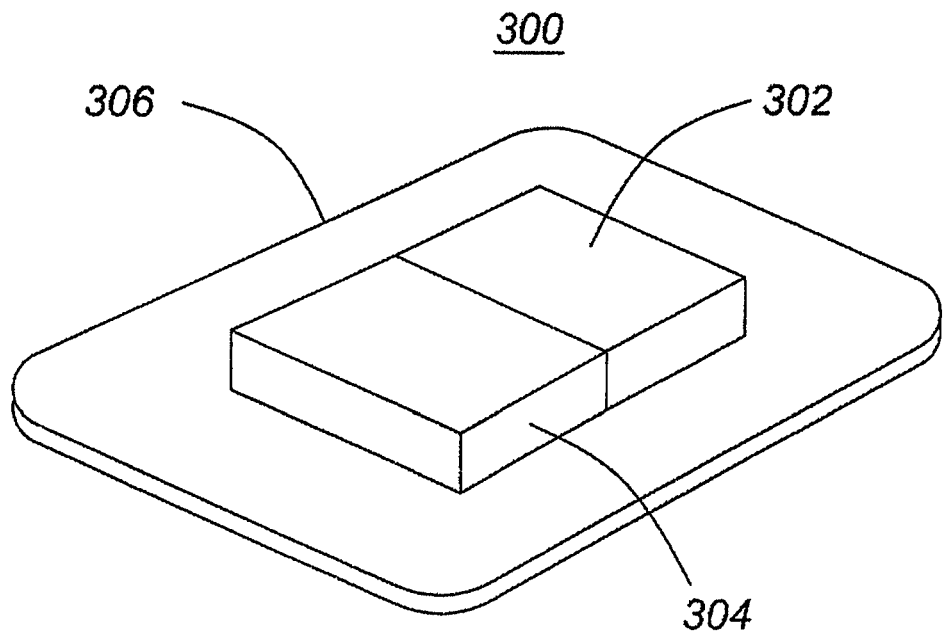
FIG. 23 is a top view of a further example of the wireless device of FIG. 1.
Figure 24:
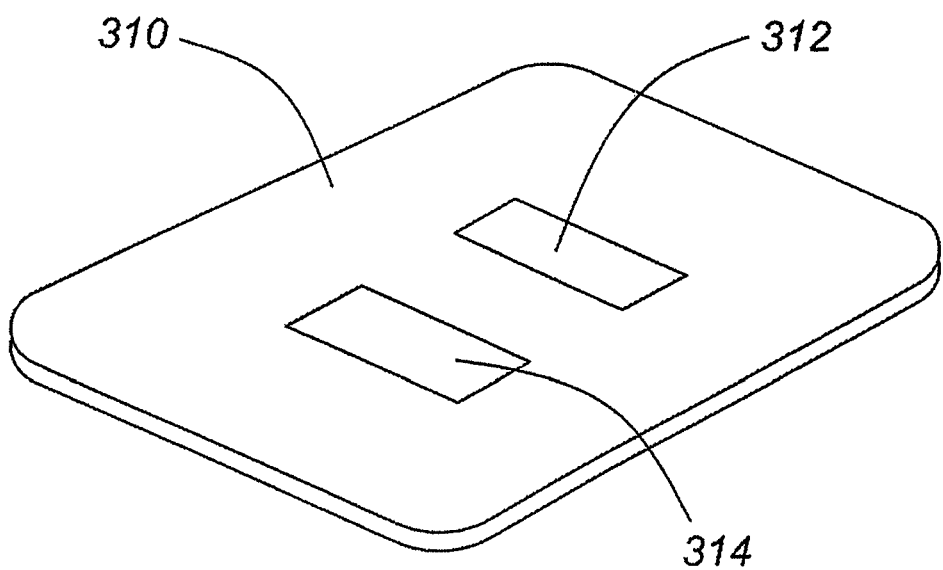
FIG. 24 is a bottom view of the wireless device of FIG. 23.
Figure 25:
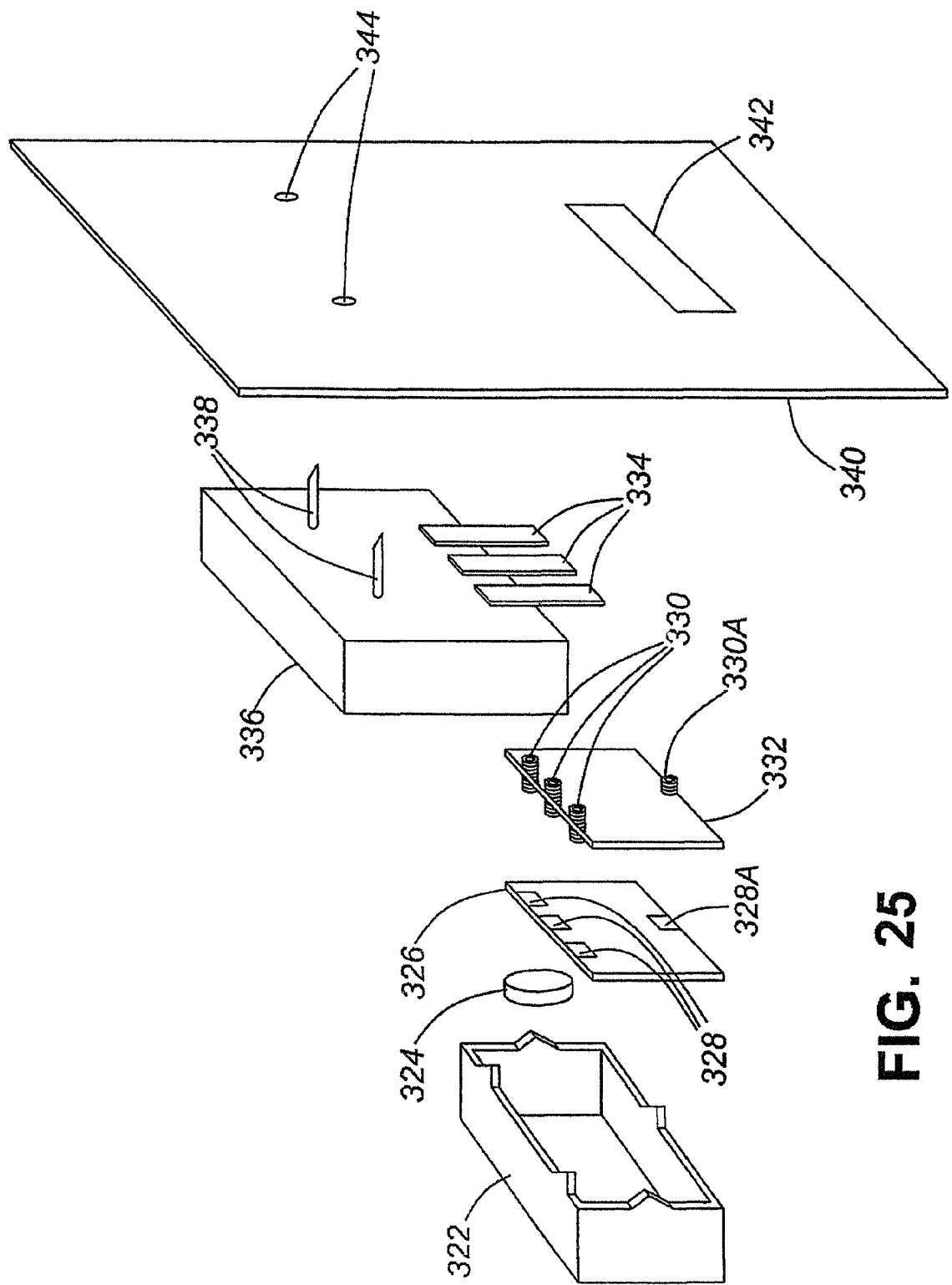
FIG. 25 is an exploded view of the wireless device of FIGS. 23-24.
Figure 26:
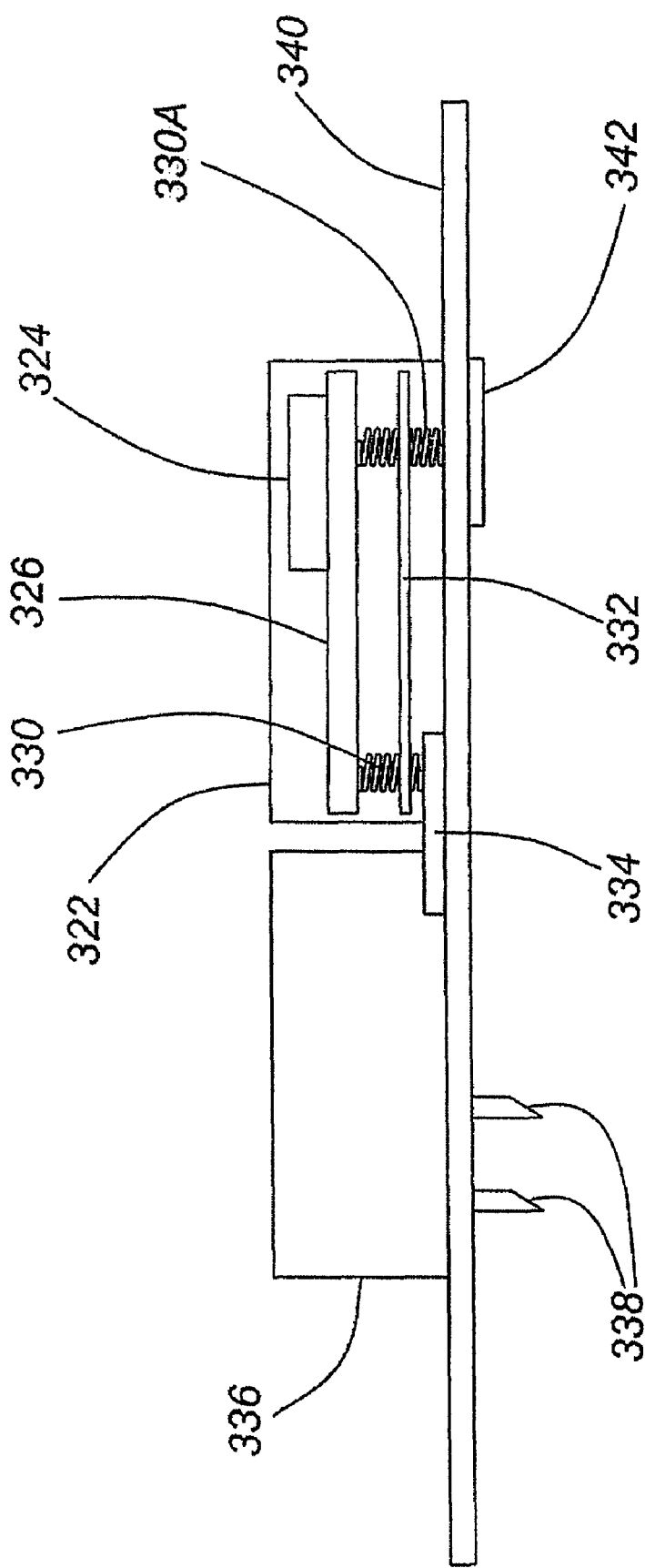
FIG. 26 is a cross section view of the wireless device of FIG. 25.

The wireless device 1 of FIG. 1 is, for example, a medical patch device having one or more contact surfaces as shown in FIGS. 23-27. The wireless device of FIGS. 23-27 is a medical patch device (hereinafter referred to as medical patch device 300). FIG. 23 illustrates an exemplary top view of the medical patch device 300. FIG. 24 illustrates an exemplary bottom view of the medical patch device 300. FIG. 25 illustrates an exemplary exploded view of the medical patch device 300. FIG. 26 illustrates an exemplary cross section view of the medical patch device 300. In the implementations of FIGS. 23-27, a conductive member (e.g., 2 of FIG. 1) is employed, for example, in or on a contact surface to which the user's body contacts for therapy or measurement purpose. An additional requirement for the medical patch device may be applied for flexibility and the ability to maintain good skin contact during movement.

The medical patch device 300 is an electronically controlled wireless device and includes a therapy or diagnostic measurement module 302, an electronic module 304 and a patch 306. The therapy or diagnostic measurement module 302 and an electronic module 304 are mounted on the patch 306.

The therapy or measurement module 302 and the electronic module 304 may be bonded to the medical patch 306 having an adhesive layer 310 that is placed on the skin. The therapy or measurement module 302 may contain drug to be delivered or may contain electrodes or other sensing elements necessary for the operation of the device. The electronic module 304 contains electronic functions of the device, and may include one or more active electronic devices that may contain the RF or wireless functions. The electronic module 304 may also include a battery for supplying power for the device operation. The wireless capability of the medical patch device 300 allows external control and or monitoring of the patch device: The therapy or measurement module 302 and the electronic module 304 may or may not be removable or replaceable.

The bottom side of the medical patch device 300 has three components: adhesive layer 310, active therapy or measurement area 312, and conductive patch 314 for wireless communications. In the area 312, the medical patch device 300 actively provides therapy or performs the medical measurement. The area 312 is associated with the therapy/measurement module 302. In one example, the electronic module 304 includes a wireless communication element and receives any wireless operation commands to operate the therapy or measurement module 302 or transmits information obtained at the therapy or measurement module 302 or the therapy or measurement area 312. The conductive patch 314 corresponds to the conductive member 2 of FIG. 1.

In use the adhesive layer 310 is applied to the skin on some part of the user's body. After activation the electronic module 304 performs the control or measurements required for function of the medical patch device 300. The conductive patch 314 couples the RF energy into the body of the user. The conductive patch 314 may be formed by, for example, but not limited to, a metal conductor, a printed or painted conductor, a conductive mesh or screen or even a section of conductive adhesive. All of these conductors may be held against the skin of the user by the adhesive layer 310. The skin under the medical patch 306 is maintained as a good electrical conductor due to skin moisture and oils, which allows the RF energy to couple into the body.

Referring to FIG. 25, "322" represents a cover (snap off); "324" represents a battery; "326" represents an electronic module with RF; "328" represents electrical contacts; "328A" represents an RF contact; "330" represents electrical contact springs; "330A" represents an RF electrical contact spring; "332" represents an interface spring holder; "334" represents electrical contacts to a therapy or measurement module; "336" represents the therapy or measurement module and corresponds to 302 of FIG. 22; "338" represents one or more therapy or measurement needles, and is related to 312 of FIG. 24; "340" represents an adhesive patch and corresponds to 310 of FIG. 24; "342" represents a conductive patch for RF coupling and corresponds to 314 of FIG. 24; and "344" represents one or more holes for the therapy or measurement needles 338.

In this instantiation the conductive patch 342 for RF coupling is located on the bottom or "skin" side of the medical patch. This conductive patch 342 makes electrical contact to the skin in normal operation. The adhesive patch 340 used to fasten the device to the skin is constructed of an insulating flexible plastic material. The medical therapy or measurement module 336 is mounted on the topside of the adhesive patch 340 with the therapy or measurement needles 338 protruding through the adhesive patch 340 to the "skin" side. The electronic module 326 and the battery 324 in this example are housed in a non-conductive housing formed by the cover 322 and the spring contact interface 332. This housing is constructed of non-conductive material and will snap into place onto the medical patch. The spring contacts 330 allow connection to the therapy or measurement unit through the electrical contacts 334 and spring contact 330A is used to make connection between the RF port of the electronic module 326 and the conductive patch 342 for RF coupling.

Referring to FIG. 26, the conductive patch 342 for RF coupling is shown on the bottom or "skin" side of the patch. The RF module is placed on the opposite side of the adhesive patch 340 that is made of a flexible plastic non-conductive material. The electrical connection between the RF transmitter/receiver of the electronic module 326 and the conductive patch 342 is accomplished by the conductive spring 330A that contacts the RF port of the electronics module 326 and the conductive patch 342. The majority of the components in the assembly are constructed of non-conductive materials and springs 330 and 330A are used to electrically interconnect the components.

In a further example, a conductive gel may be used to provide a good electrical contact with the body. The conductive gel may be part of a pad or a patch. The gel pad is, for example, a small package of conductive gel and may be inserted separately between the conductor on the patch and the skin. This package of the conductive gel may also be constructed as part of the patch device and may not necessarily be a separated component. The gel pad may be directly connected to the adhesive layer (e.g., 310 of FIG. 24, 340 of FIG. 25) or may be inserted between the skin and the conductive patch (e.g., 314 of FIG. 24, 342 of FIG. 25) that is on the adhesive layer.

Figure 27:
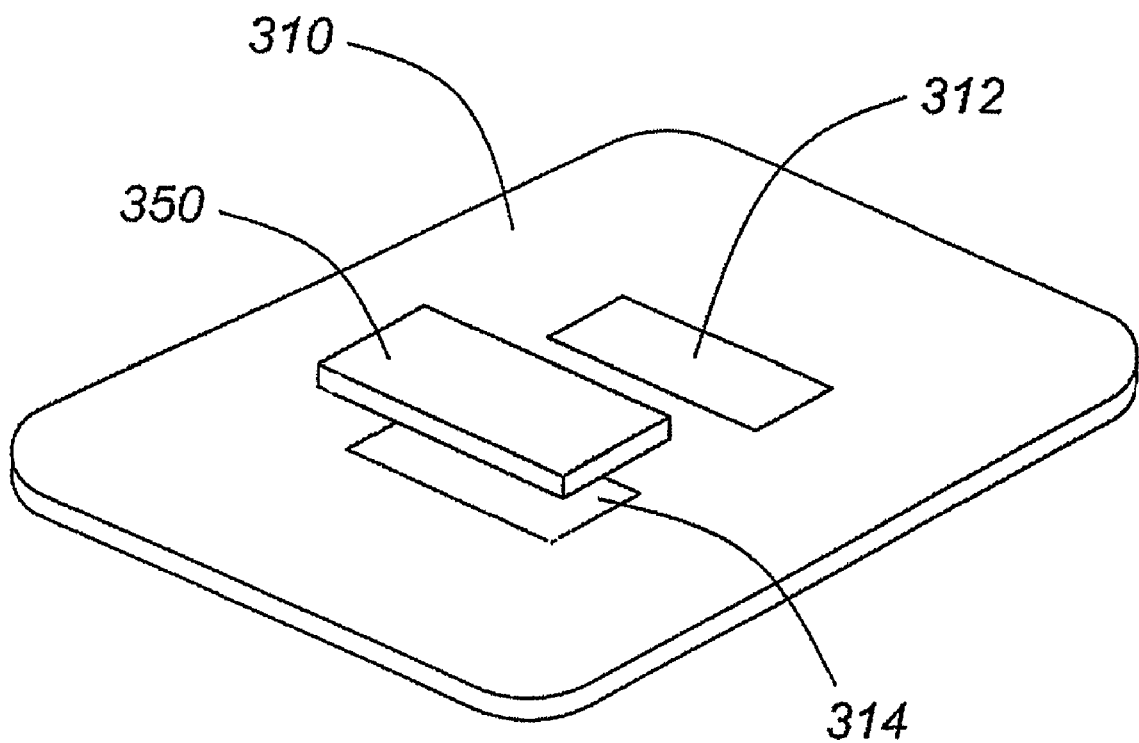
FIG. 27 is another exemplary bottom view of the wireless device of FIG. 23.

Referring to FIG. 27, there is illustrated another exemplary bottom view of the medical patch device 300 of FIG. 23. In FIG. 27, a conductive gel patch 350 is placed on the conductive patch 314 for wireless communications and is in contact with the skin of the user. The conductive gel patch 350 ensures good electrical contact with the skin and maintains good contact even in situations where the medical patch is flexible. The conductive gel patch 350 enhances conductivity.

The conductive gel may be applied to any other applications for wireless communications, such as any other hearing devices, personal wireless entertainment devices.

The wireless device 1 of FIG. 1 may be a portable wireless device (e.g., handheld wireless device). Similarly to the hearing aids and the medical patch devices described above, a conductive member on the handheld wireless device is connected to the RF port of the wireless handheld device and is also in contact with the user. This allows RF energy to couple onto the body of the user for conduction or radiation.

The wireless handheld device may be physically large enough or shaped in such a way it may contain an effective antenna, or it may be large enough that the power or space limitations may not restrict the performance of the wireless handheld device. On the other hand, it may have size and power constraints similar to those of hearing aids or medical patch devices. In any of the above situations, the RF energy coupled to the body of the user can provide an efficient wireless antenna or provide a conduction path to another body worn device or another body who wears a wireless device. In this implementation, the user of the wireless handheld device directly contacts to the wireless handheld device without gloves or any other material that may prevent electrical contact between the body of the user and the conductive member of the wireless handheld device.

Figure 28:
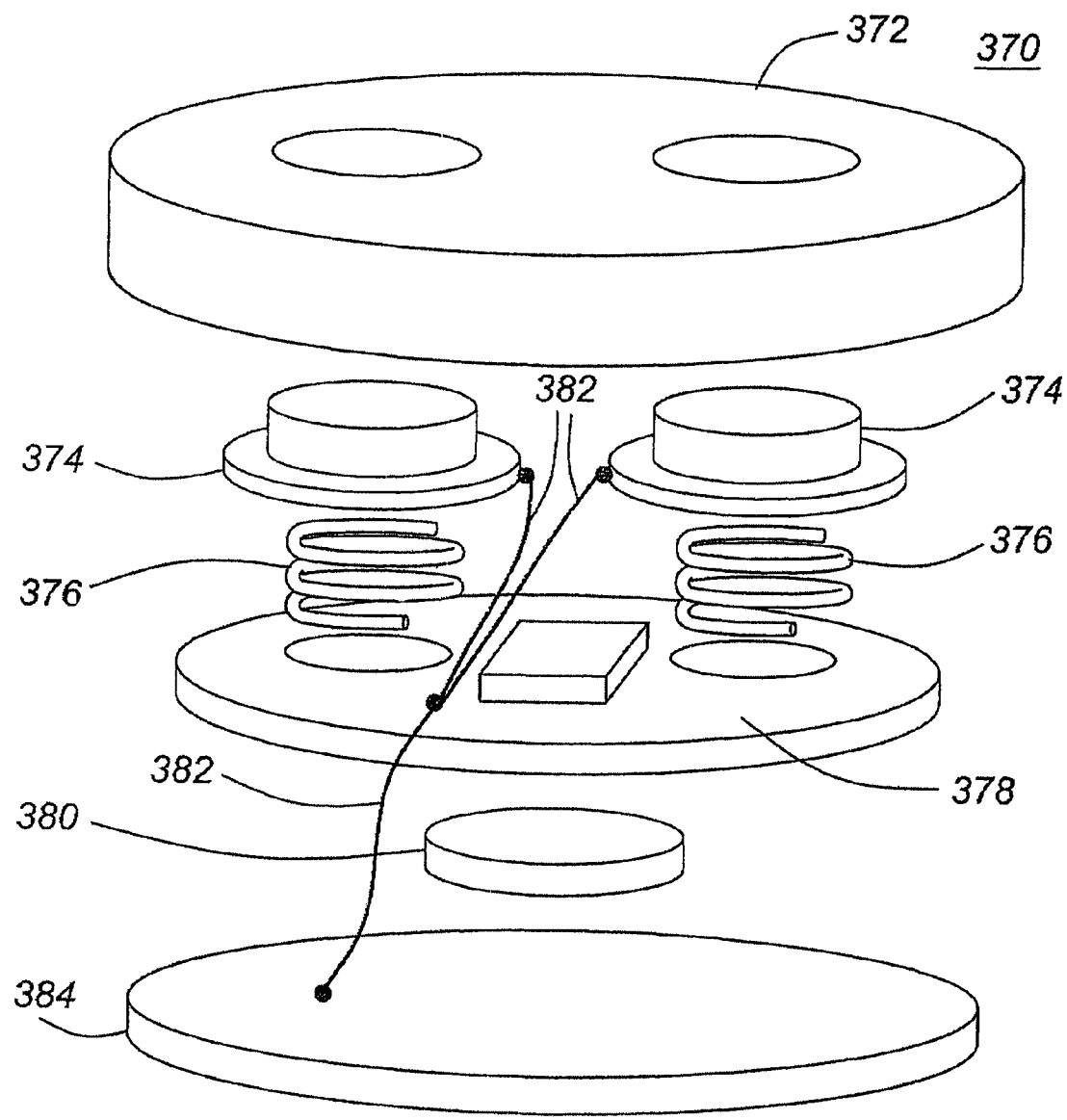
FIG. 28 is an exploded view of a further example of the wireless device of FIG. 1.

Referring to FIG. 28, there is provided an exploded view of a further example of the wireless device 1 of FIG. 1. The wireless device 370 of FIG. 28 is a wireless handheld remote controller with a conductive member to couple the RF energy into or out of the user's body (hereinafter referred to as handheld remote controller 370). The handheld remote controller 370 corresponds to the wireless device 1 of FIG. 1.

In FIG. 28, "372" represents a non-conductive case (body); "374" represents a push button; "376" represents a spring; "378" represents an electronic module with RF; "380" represents a battery; "382" represents wires to the conductive buttons 374 and a conductive back; "384" represents a conductive back (back cover).

The body 372 is constructed of a non-conductive material with the conductive back cover 384. The back 384 may be constructed from a metallic component, conductive plastic, or a conductive plate, mesh or conductive coating. The body 372 may be constructed of a non-conductive material with a conductive side or top cover.

The buttons 374 may be made of a conductive material. The electronic assembly is mounted within the housing in such a manner to electrically isolate the assembly from the conductive back 384 and the conductive buttons 374. Insulated conductors are used to connect the RF port of the electronic module 378 to the module back 384 and or the conductive buttons 374. The conductive buttons 374 may be constructed in a manner that allows the conductive portion to protrude through the top cover 372 but insulated on the lower sides where the lower sides of the buttons contact the switches that they activate. The battery 380 is mounted in such a manner to prevent electrical contact from its positive or negative terminal.

Figure 29:
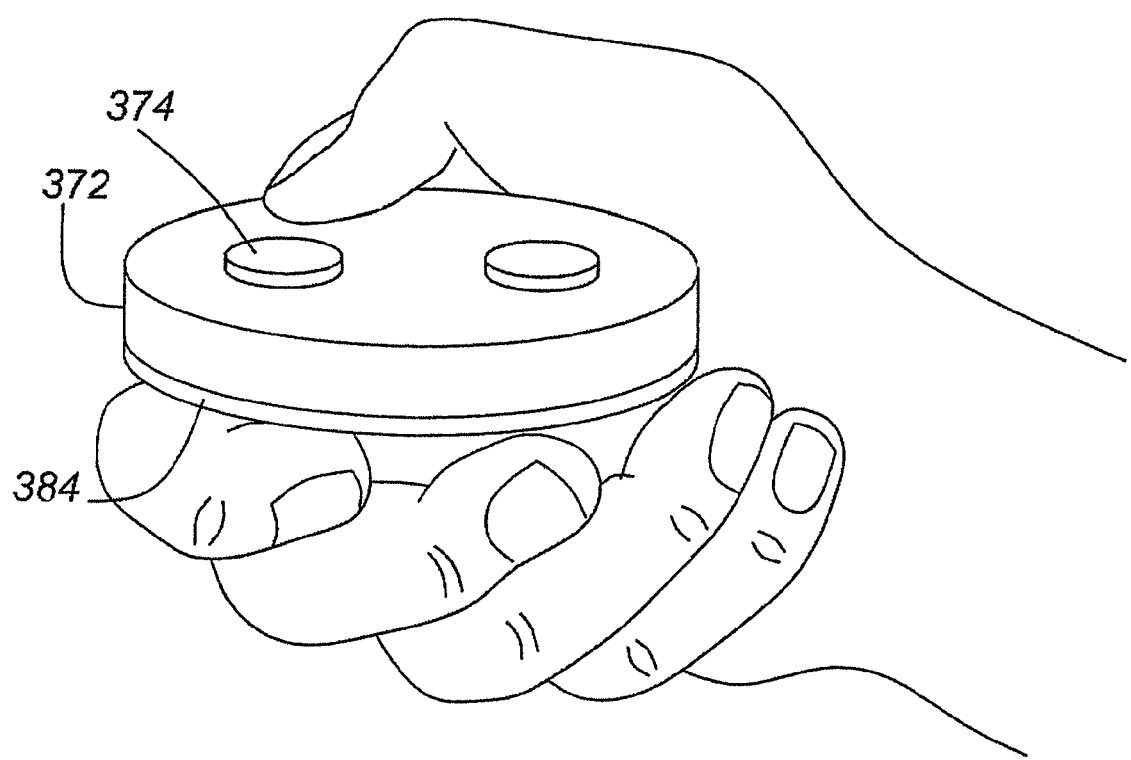
FIG. 29 is a view of the wireless device of FIG. 28, relative to the user's right hand.

Referring to FIG. 29, there is illustrated an exemplary configuration of the handheld remote controller 370 of FIG. 28. The conductive back 384 rests on a number of the user's fingers and part of the palm. If the buttons 374 are also conductive, the users thumb can also be connected to the RF port of the wireless electronic module (e.g., 378 of FIG. 28) contained within the remote. The buttons 374 may be any mechanical, electrical or magnet switches, and may include touch sensors. By pushing the button 374, the handheld remote controller 370 or any part of the functionality of the handheld controller 370 is activated.

When the button 374 is pressed and the handheld remote controller is acting as an RF receiver or a RF transmitter the users' fingers or palm will be in contact to the (conductive) buttons 374 or the conductive patch on the side or the bottom of the device (e.g. back 384). This allows the RF energy to be coupled into or out of the users hand. If the user has another body worn wireless device that uses this body coupled approach for the antenna, the RF energy will likely use the body conduction for the RF transmission path. If the hand held user is not wearing a body worn device the users' body will then act as a RF radiator.

When the button 372 and a part (or entire) of the housing of the handheld remote controller 370 are conductive, the contact between the handheld remote controller and the user will be enhanced as pressure is applied to depress the device's buttons.

The present invention has been described with regard to one or more embodiments. However, it will be apparent to persons skilled in the art that a number of variations and modifications can be made without departing from the scope of the invention as defined in the claims.

What is claimed is:

1. A hearing device with wireless communications, the hearing device comprising:
   a Radio Frequency (RF) module including an RF input, an RF output or a combination;
   a shell for housing the RF module; and
   a coupler coupled to the shell, including:
   a conductive member moldable to a user and forming continuous conductive contact to at least a part of the user's body, RF energy coupling into and/or out of the user's body via the conductive member; and
   a connection member for electrically coupling the conductive member to the RF module,
   the hearing device being removably attached to or inserted into the ear of the user for use.

2. A hearing device as claimed in claim 1, wherein the connection member includes an electrode or a contact having a conductive material.

3. A hearing device as claimed in claim 1, wherein the connection member is insulated.

4. A hearing device as claimed in claim 1, wherein the hearing device comprises one or more electrical components, and wherein the conductive member is isolated from the one or more than one electrical components.

5. A hearing device as claimed in claim 4, wherein the one or more than one electrical components are isolated by a non-conductive member.

6. A hearing device as claimed in claim 4, further comprising a connection for communicating between the RF module and the at least one of the electrical components while maintaining the isolation between the conductive member and the at least one of the electrical components.

7. A hearing device as claimed in claim 1, wherein the RF module includes the RF port of a wireless transmitter, the RF port of a wireless receiver, or the RF port of a wireless transceiver's antenna.

8. A hearing device as claimed in claim 1, wherein the RF energy is coupled into the user's body through the coupler such that the user's body acts as a conductor of the RF energy.

9. A hearing device as claimed in claim 1, wherein the RF energy is coupled out of the user's body through the coupler such that the user's body acts as a pseudo antenna.

10. A hearing device as claimed in claim 1, wherein the conductive member includes a metallic, a conductive elastomer, a conductive plastic, a conductive patch, a conductive paint, a conductive print, a conductive coating, a conductive mesh, a conductive web, a conductive screen, a conductive liquid, a conductive gel, or combinations thereof.

11. A hearing device as claimed in claim 1, wherein the conductive member comprises a contact surface custom molded for each user.

12. A hearing device as claimed in claim 1, wherein the shell is a custom molded shell including an outer surface forming the continuous contact to the user's body and an interior surface facing to the RF module, and wherein the interior surface includes a non-conductive section.

13. A hearing device as claimed in claim 1, wherein the shell includes a custom molded shell for an earpiece.

14. A hearing device as claimed in claim 13, wherein the shell for housing the RF module is coupled to the earpiece, and wherein the custom molded shell includes a non-conductive material.

15. A hearing device as claimed in claim 1, further comprising a body coupling member for fitting at least a part of the hearing device into the user's body, and wherein the conductive member is molded into the body coupling member.

16. A hearing device as claimed in claim 15, wherein the body coupling member is attached to the shell.

17. A hearing device as claimed in claim 16, wherein the shell includes a non-conductive outer surface and a non-conductive interior surface facing to the RF module.

18. A hearing device as claimed in claim 15, wherein the body coupling member is made of a moldable flexible or elastic member.

19. A hearing device as claimed in claim 15, wherein the body coupling member is an earpiece, ear clip, a frame, a headphone, an earphone, an earbud, a stereophone, a headset, an elastomer, or combinations thereof.

20. A system as claimed in claim 1, wherein the system is a portable wireless device worn on the user's body.

21. A system as claimed in claim 1, wherein the system is a medical patch device worn on the user's body for a therapy or medical measurement or operation.

22. A system as claimed in claim 21, wherein the medical patch device includes a therapy or measurement module and an electrical contact member for connecting the therapy or measuring module to the RF module.

23. A system as claimed in claim 21, wherein the medical patch device includes an adhesive layer applied to the user's body, and wherein the conductive member is on or in the adhesive layer.

24. A system as claimed in claim 23, wherein the therapy or measurement module and the RF module are placed on the opposite side of the adhesive layer.

25. A system as claimed in claim 23, wherein adhesive layer is a flexible plastic non-conductive material.

26. A system as claimed in claim 1, further comprising a conductive gel member in or on the conductive member, and wherein the conductive gel member being in directly contact with the user's body.

27. A system as claimed in claim 1, wherein the conductive member includes a plurality of conductive layers, at least one of the layers being in physical contact or proximity with the user's body.

28. A system as claimed in claim 1, wherein no ground connection is made at the conductive member.

29. A system as claimed in claim 1, further comprising a battery, and wherein the coupler is isolated from the battery.

30. A system as claimed in claim 1, wherein the conductive member is in proximity with the user's body when the system is in operation.

31. A hearing device with wireless communications, the hearing device comprising:
    a wireless communication device including:
    a Radio Frequency (RF) module having an RF port for RF communications; and
    a conductive member moldable to a user and forming a continuous conductive contact to at least a part of the user's body, the RF port coupling to the at least a part of the user's body via the conductive member so that the at least a part of the user's body is used as a conductive path to an external wireless communication device,
    the hearing device being removably attached to or inserted into the ear of the user for use.

32. A hearing device as claimed in claim 31, wherein the external communication device comprises a coupler conductive coupling to the conductive path directly or via another user's body.

33. A hearing device as claimed in claim 31, wherein the RF port comprises a port for an RF receiver, and wherein the RF port receives a communication signal output from the external wireless communication device via the at least a part of the user's body.

34. A hearing device as claimed in claim 31, wherein the RF port comprises a port for an RF transmitter, and wherein a communication signal output from the RF port is transmitted to the external communication device via the at least a part of the user's body.

35. A portable hearing device with wireless communications, the hearing device comprising:
    a wireless communication device including:
    a Radio Frequency (RF) module including an RF port for RF communications; and
    a conductive member moldable to a user and forming a continuous conductive contact to at least a part of the user's body, the RF port coupling to the at least a part of the user's body via the conductive member so that the at least a part of the user's body is used as an RF antenna for the wireless communications with an external wireless communication device,
    the hearing device being removably attached to or inserted into the ear of the user for use.

36. A hearing device as claimed in claim 35, wherein the RF port comprises a port for an RF receiver, and wherein the RF port receives a communication signal output from the external wireless communication device via the at least a part of the user's body.

37. A hearing device as claimed in claim 35, wherein the RF port module comprises a port for an RF transmitter, and wherein a communication signal output from the RF port is radiated to the external wireless communication device via the at least a part of the user's body.

* * * * *